US012318552B2

(12) United States Patent
Simiele et al.

(10) Patent No.: US 12,318,552 B2
(45) Date of Patent: Jun. 3, 2025

(54) COLLAPSIBLE THIN-WALLED VALVE FOR DRAINAGE CONTROL

(71) Applicant: C. R. Bard, Inc., Franklin Lakes, NJ (US)

(72) Inventors: David M. Simiele, Roswell, GA (US); Jason Jishen Cheng, Avondale Estates, GA (US); Varad Chavan, Maharashtra (IN); Rohit Sinha, Lawrenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/526,994

(22) Filed: Nov. 15, 2021

(65) Prior Publication Data

US 2022/0152345 A1    May 19, 2022

Related U.S. Application Data

(60) Provisional application No. 63/115,489, filed on Nov. 18, 2020, provisional application No. 63/115,501, filed on Nov. 18, 2020.

(51) Int. Cl.
*A61M 25/00* (2006.01)
*F16K 7/07* (2006.01)
*G05D 16/20* (2006.01)

(52) U.S. Cl.
CPC ........... *A61M 25/0017* (2013.01); *F16K 7/07* (2013.01); *G05D 16/2066* (2013.01);
(Continued)

(58) Field of Classification Search
CPC ........ A61M 1/742; A61M 1/743; A61M 1/83; A61M 2025/0019; A61M 2025/0025;
(Continued)

(56) References Cited

U.S. PATENT DOCUMENTS

| 3,114,916 A | 12/1963 | Hadley |
| 3,583,401 A | 6/1971 | Vailiancourt et al. |

(Continued)

FOREIGN PATENT DOCUMENTS

| CN | 106955208 A | 7/2017 |
| CN | 116650740 A | 8/2023 |

(Continued)

OTHER PUBLICATIONS

PCT/US2022/049418 filed Nov. 9, 2022 International Search Report and Written Opinion dated Feb. 10, 2023.

(Continued)

*Primary Examiner* — Sarah Al Hashimi
*Assistant Examiner* — Jihad Dakkak
(74) *Attorney, Agent, or Firm* — Rutan & Tucker LLP

(57) ABSTRACT

Embodiments disclosed herein are directed to a drainage control system including, a tubular body with a tubular body lumen extending from a distal end to a proximal end and a collapsible tube disposed within the tubular body lumen, the collapsible tube including a collapsible tube lumen extending from a distal end to a proximal end of the collapsible tube. The collapsible tube can be attached to the tubular body, such that fluid flow through the tubular body lumen flows through the collapsible tube lumen. The tubular body can include a valve that is actuatable between a first configuration wherein fluid flow is allowed through the tubular body lumen and a second configuration wherein fluid flow is prevented through the tubular body lumen. An airflow source can be coupled to the valve such that pressure from the airflow source actuates the valve.

17 Claims, 14 Drawing Sheets

(52) U.S. Cl.
CPC ............... *A61M 2025/0019* (2013.01); *A61M 2205/3337* (2013.01); *A61M 2205/3344* (2013.01)

(58) Field of Classification Search
CPC .. A61M 2202/0496; A61M 2205/3344; A61M 2205/3355; A61M 2210/1078; A61M 25/0017; A61M 27/002; A61M 27/006; A61M 39/227; A61M 39/228; A61B 10/0045; A61B 10/007; F16K 7/07; G05D 16/2066
See application file for complete search history.

(56) References Cited

U.S. PATENT DOCUMENTS

| | | | |
|---|---|---|---|
| 3,598,124 | A | 8/1971 | Andersen et al. |
| 3,661,143 | A | 5/1972 | Henkin |
| 3,861,394 | A | 1/1975 | Villari |
| 3,901,235 | A | 8/1975 | Patel et al. |
| 3,955,574 | A | 5/1976 | Rubinstein |
| 4,084,593 | A | 4/1978 | Jarund |
| 4,265,243 | A | 5/1981 | Taylor |
| 4,305,403 | A | 12/1981 | Dunn |
| 4,315,506 | A | 2/1982 | Kayser et al. |
| 4,360,933 | A | 11/1982 | Kimura et al. |
| 4,465,485 | A | 8/1984 | Kashmer et al. |
| 4,490,144 | A | 12/1984 | Steigerwald |
| 4,531,939 | A | 7/1985 | Izumi |
| 4,556,997 | A | 12/1985 | Takamiya et al. |
| 4,631,061 | A | 12/1986 | Martin |
| 4,654,029 | A | 3/1987 | D'Antonio |
| 4,747,166 | A | 5/1988 | Kuntz |
| 4,810,242 | A | 3/1989 | Sundblom et al. |
| 4,819,684 | A | 4/1989 | Zaugg et al. |
| 4,872,579 | A | 10/1989 | Palmer |
| 4,880,411 | A | 11/1989 | Fangrow, Jr. et al. |
| 4,990,137 | A | 2/1991 | Graham |
| 5,002,528 | A | 3/1991 | Palestrant |
| 5,071,411 | A | 12/1991 | Hillstead |
| 5,186,431 | A | 2/1993 | Tamari |
| 5,242,404 | A | 9/1993 | Conley et al. |
| 5,318,550 | A | 6/1994 | Cermak et al. |
| 5,359,233 | A | 10/1994 | Mumper et al. |
| 5,405,319 | A * | 4/1995 | Abell ................. A61M 3/0208 604/27 |
| RE35,707 | E | 12/1997 | Takamiya et al. |
| 5,738,656 | A | 4/1998 | Wagner et al. |
| 5,813,842 | A * | 9/1998 | Tamari ..................... F16K 7/07 417/63 |
| 5,894,608 | A | 4/1999 | Birbara |
| 6,007,521 | A | 12/1999 | Bidwell et al. |
| 6,106,506 | A * | 8/2000 | Abell ........................ F16K 7/07 604/257 |
| 6,183,454 | B1 | 2/2001 | Levine et al. |
| 8,266,741 | B2 | 9/2012 | Penninger et al. |
| 8,337,475 | B2 | 12/2012 | Christensen et al. |
| 8,475,419 | B2 | 7/2013 | Eckermann |
| 8,512,301 | B2 | 8/2013 | Ma |
| 9,814,866 | B1 | 11/2017 | Goswami |
| 10,391,275 | B2 | 8/2019 | Burnett et al. |
| 10,426,919 | B2 | 10/2019 | Erbey, II et al. |
| 10,506,965 | B2 | 12/2019 | Cooper et al. |
| 10,737,057 | B1 | 8/2020 | Mikhail et al. |
| 10,772,998 | B2 | 9/2020 | Luxon et al. |
| 2002/0000253 | A1 | 1/2002 | Fillmore et al. |
| 2002/0161317 | A1 | 10/2002 | Risk et al. |
| 2003/0078638 | A1 | 4/2003 | Voorhees et al. |
| 2004/0176746 | A1 | 9/2004 | Forral |
| 2004/0230181 | A1 | 11/2004 | Cawood |
| 2004/0236292 | A1 | 11/2004 | Tazoe et al. |
| 2004/0254547 | A1 | 12/2004 | Okabe et al. |
| 2005/0197647 | A1 | 9/2005 | Dolliver et al. |
| 2005/0209585 | A1 | 9/2005 | Nord et al. |
| 2005/0245898 | A1 | 11/2005 | Wright et al. |
| 2005/0256460 | A1 | 11/2005 | Rome et al. |
| 2005/0261619 | A1 | 11/2005 | Gay |
| 2006/0015190 | A1 | 1/2006 | Robertson |
| 2006/0079854 | A1 | 4/2006 | Kay et al. |
| 2006/0155260 | A1 | 7/2006 | Blott et al. |
| 2006/0235353 | A1 | 10/2006 | Gelfand et al. |
| 2006/0270971 | A1 | 11/2006 | Gelfand et al. |
| 2006/0271019 | A1 | 11/2006 | Stoller et al. |
| 2007/0005002 | A1 | 1/2007 | Millman et al. |
| 2007/0078444 | A1 | 4/2007 | Larsson |
| 2007/0142729 | A1 * | 6/2007 | Pfeiffer ............. A61M 25/0097 600/487 |
| 2007/0272311 | A1 | 11/2007 | Trocki et al. |
| 2008/0156092 | A1 | 7/2008 | Boiarski |
| 2008/0281254 | A1 | 11/2008 | Humayun et al. |
| 2009/0157016 | A1 | 6/2009 | Adahan |
| 2009/0157040 | A1 | 6/2009 | Jacobson et al. |
| 2009/0326483 | A1 | 12/2009 | Green |
| 2010/0106116 | A1 | 4/2010 | Simmons et al. |
| 2010/0130949 | A1 | 5/2010 | Garcia |
| 2011/0060300 | A1 | 3/2011 | Weig et al. |
| 2012/0036638 | A1 | 2/2012 | Penninger et al. |
| 2012/0323144 | A1 * | 12/2012 | Coston ..................... A61M 1/83 600/581 |
| 2013/0218106 | A1 * | 8/2013 | Coston ..................... A61M 1/83 604/317 |
| 2014/0053841 | A1 | 2/2014 | Ratner |
| 2014/0200558 | A1 | 7/2014 | McDaniel |
| 2014/0200588 | A1 | 7/2014 | Anderson et al. |
| 2015/0126975 | A1 | 5/2015 | Wuthier |
| 2015/0290448 | A1 | 10/2015 | Pavlik |
| 2016/0135982 | A1 | 5/2016 | Garcia |
| 2016/0183819 | A1 | 6/2016 | Burnett et al. |
| 2016/0310711 | A1 | 10/2016 | Luxon et al. |
| 2017/0014617 | A1 | 1/2017 | Huici |
| 2017/0072125 | A1 * | 3/2017 | Wallenås ............... A61M 1/282 |
| 2017/0136209 | A1 * | 5/2017 | Burnett ................... A61M 1/84 |
| 2017/0143566 | A1 | 5/2017 | Elku et al. |
| 2017/0241978 | A1 | 8/2017 | Duval |
| 2017/0312114 | A1 | 11/2017 | Glithero |
| 2018/0015251 | A1 | 1/2018 | Lampotang et al. |
| 2018/0071441 | A1 | 3/2018 | Croteau et al. |
| 2018/0104391 | A1 | 4/2018 | Luxon et al. |
| 2018/0110456 | A1 | 4/2018 | Cooper et al. |
| 2018/0125697 | A1 | 5/2018 | Ferrera |
| 2018/0177458 | A1 | 6/2018 | Burnett et al. |
| 2018/0235523 | A1 | 8/2018 | Sauder |
| 2018/0245699 | A1 | 8/2018 | Lee |
| 2018/0360424 | A1 | 12/2018 | Yurek et al. |
| 2019/0009021 | A1 | 1/2019 | Nelson et al. |
| 2019/0009023 | A1 | 1/2019 | Diperna et al. |
| 2019/0030264 | A1 | 1/2019 | Herskovic et al. |
| 2019/0038451 | A1 | 2/2019 | Harvie |
| 2019/0046102 | A1 | 2/2019 | Kushnir et al. |
| 2019/0126006 | A1 | 5/2019 | Rehm et al. |
| 2019/0143094 | A1 | 5/2019 | DeMeritt |
| 2019/0151610 | A1 | 5/2019 | Fletter |
| 2019/0343445 | A1 | 11/2019 | Burnett et al. |
| 2020/0000979 | A1 | 1/2020 | Myers |
| 2020/0061281 | A1 | 2/2020 | Desouza et al. |
| 2020/0315837 | A1 | 10/2020 | Radl et al. |
| 2021/0077007 | A1 | 3/2021 | Jouret et al. |
| 2022/0160949 | A1 | 5/2022 | Simiele et al. |
| 2022/0176031 | A1 | 6/2022 | Cheng et al. |
| 2022/0193366 | A1 | 6/2022 | Cheng et al. |
| 2022/0218890 | A1 | 7/2022 | Chavan |
| 2022/0218973 | A1 | 7/2022 | Chavan et al. |
| 2022/0218974 | A1 | 7/2022 | Chavan et al. |
| 2022/0273213 | A1 | 9/2022 | Sokolov et al. |
| 2022/0287689 | A1 | 9/2022 | Johannes |
| 2022/0305189 | A1 | 9/2022 | Chavan et al. |
| 2022/0330867 | A1 | 10/2022 | Conley et al. |
| 2022/0362080 | A1 | 11/2022 | McCorquodale et al. |
| 2022/0409421 | A1 | 12/2022 | Hughett et al. |
| 2023/0013353 | A1 | 1/2023 | Chavan et al. |
| 2023/0030637 | A1 | 2/2023 | Gloeckner et al. |
| 2023/0054937 | A1 | 2/2023 | Chancy et al. |
| 2023/0083906 | A1 | 3/2023 | Jones et al. |
| 2023/0310837 | A1 | 10/2023 | Gamsizlar et al. |

(56) References Cited

U.S. PATENT DOCUMENTS

| | | |
|---|---|---|
| 2024/0033404 A1 | 2/2024 | Ishikawa |
| 2024/0238500 A1 | 7/2024 | Simiele et al. |
| 2024/0307604 A1 | 9/2024 | Chavan |
| 2025/0009578 A1 | 1/2025 | Chancy et al. |
| 2025/0018147 A1 | 1/2025 | Rehm |
| 2025/0018149 A1 | 1/2025 | Cheng et al. |
| 2025/0025617 A1 | 1/2025 | Chavan et al. |
| 2025/0025620 A1 | 1/2025 | Cheng et al. |
| 2025/0040848 A1 | 2/2025 | Lai et al. |

FOREIGN PATENT DOCUMENTS

| | | |
|---|---|---|
| EP | 1872752 A1 | 1/2008 |
| EP | 2417955 A2 | 2/2012 |
| EP | 2730299 A1 | 5/2014 |
| WO | 2009/026237 A1 | 2/2009 |
| WO | 2012016179 A1 | 2/2012 |
| WO | 2015019056 A1 | 2/2015 |
| WO | 2015/105916 A1 | 7/2015 |
| WO | 2016012494 A1 | 1/2016 |
| WO | 2017177068 A1 | 10/2017 |
| WO | 2018136306 A1 | 7/2018 |
| WO | 2018191193 A1 | 10/2018 |
| WO | 2019004854 A1 | 1/2019 |
| WO | 2020033752 A1 | 2/2020 |
| WO | 2021154427 A1 | 8/2021 |
| WO | 2022/159333 A1 | 7/2022 |
| WO | 2022/251425 A1 | 12/2022 |
| WO | 2023086394 A1 | 5/2023 |

OTHER PUBLICATIONS

U.S. Appl. No. 17/556,942, filed Dec. 20, 2021 Non-Final Office Action dated Jan. 31, 2023.
PCT/US2022/012373 filed Jan. 13, 2022 International Search Report and Written Opinion dated Apr. 19, 2022.
PCT/US2020/066707 filed Dec. 22, 2020 International Search Report and Written Opinion dated Apr. 15, 2021.
U.S. Appl. No. 17/532,454, filed Nov. 22, 2021 Non-Final Office Action dated Mar. 22, 2023.
U.S. Appl. No. 17/542,060, filed Dec. 3, 2021 Non-Final Office Action dated Jun. 27, 2023.
U.S. Appl. No. 17/556,942, filed Dec. 20, 2021 Final Office Action dated Jul. 12, 2023.
U.S. Appl. No. 17/561,458, filed Dec. 23, 2021 Non-Final Office Action dated Jun. 16, 2023.
U.S. Appl. No. 17/561,504, filed Dec. 23, 2021 Final Office Action dated Jul. 19, 2023.
U.S. Appl. No. 17/561,504, filed Dec. 23, 2021 Non-Final Office Action dated Mar. 14, 2023.
U.S. Appl. No. 17/863,898, filed Jul. 13, 2022 Non-Final Office Action dated Jul. 17, 2023.
U.S. Appl. No. 17/902,705, filed Sep. 2, 2022 Non-Final Office Action dated May 24, 2023.
U.S. Appl. No. 17/373,568, filed Jul. 12, 2021 Non-Final Office Action dated Nov. 9, 2023.
U.S. Appl. No. 17/532,454, filed Nov. 22, 2021 Final Office Action dated Sep. 27, 2023.
U.S. Appl. No. 17/556,942, filed Dec. 20, 2021 Advisory Action dated Sep. 1, 2023.
U.S. Appl. No. 17/556,942, filed Dec. 20, 2021 Non-Final Office Action dated Nov. 3, 2023.
U.S. Appl. No. 17/561,458, filed Dec. 23, 2021 Final Office Action dated Sep. 12, 2023.
U.S. Appl. No. 17/902,705, filed Sep. 2, 2022 Advisory Action dated Oct. 19, 2023.
U.S. Appl. No. 17/902,705, filed Sep. 2, 2022 Final Office Action dated Aug. 17, 2023.
U.S. Appl. No. 17/373,568, filed Jul. 12, 2021 Notice of Allowance dated Apr. 26, 2024.
U.S. Appl. No. 17/532,454, filed Nov. 22, 2021 Notice of Allowance dated Dec. 8, 2023.
U.S. Appl. No. 17/542,060, filed Dec. 3, 2021 Non-Final Office Action dated Nov. 28, 2023.
U.S. Appl. No. 17/542,060, filed Dec. 3, 2021 Notice of Allowance dated Jun. 3, 2024.
U.S. Appl. No. 17/556,942, filed Dec. 20, 2021 Final Office Action dated Apr. 4, 2024.
U.S. Appl. No. 17/556,942, filed Dec. 20, 2021 Notice of Allowance dated Jun. 26, 2024.
U.S. Appl. No. 17/561,458, filed Dec. 23, 2021 Notice of Allowance dated Dec. 6, 2023.
U.S. Appl. No. 17/561,504, filed Dec. 23, 2021 Non-Final Office Action dated Nov. 27, 2023.
U.S. Appl. No. 17/561,504, filed Dec. 23, 2021 Notice of Allowance dated Jan. 22, 2024.
U.S. Appl. No. 17/796,604, filed Jul. 29, 2022 Notice of Allowance dated May 1, 2024.
U.S. Appl. No. 17/863,898, filed Jul. 13, 2022 Advisory Action dated Jan. 30, 2024.
U.S. Appl. No. 17/863,898, filed Jul. 13, 2022 Final Office Action dated Nov. 22, 2023.
U.S. Appl. No. 17/863,898, filed Jul. 13, 2022 Non-Final Office Action dated Mar. 11, 2024.
U.S. Appl. No. 17/902,705, filed Sep. 2, 2022 Final Office Action dated May 22, 2024.
U.S. Appl. No. 17/902,705, filed Sep. 2, 2022 Non-Final Office Action dated Dec. 7, 2023.
U.S. Appl. No. 17/571,254, filed Jan. 7, 2022 Restriction Requirement dated Oct. 4, 2024.
U.S. Appl. No. 17/863,898, filed Jul. 13, 2022 Advisory Action dated Oct. 28, 2024.
U.S. Appl. No. 17/863,898, filed Jul. 13, 2022 Final Office Action dated Aug. 22, 2024.
U.S. Appl. No. 17/902,705, filed Sep. 2, 2022 Advisory Action dated Aug. 1, 2024.
U.S. Appl. No. 17/902,705, filed Sep. 2, 2022 Notice of Allowance dated Sep. 18, 2024.
U.S. Appl. No. 17/863,898, filed Jul. 13, 2022 Non-Final Office Action dated Dec. 2, 2024.
U.S. Appl. No. 18/274,157 filed Jul. 25, 2023 Non-Final Office Action dated Jan. 17, 2025.
U.S. Appl. No. 17/571,254, filed Jan. 7, 2022 Non-Final Office Action dated Feb. 13, 2025.
U.S. Appl. No. 18/674,694, filed May 24, 2024 Non-Final Office Action dated Mar. 3, 2025.

* cited by examiner

COLLAPSIBLE THIN-WALLED VALVE FOR DRAINAGE CONTROL

PRIORITY

This application claims the benefit of priority to U.S. Provisional Application No. 63/115,489, filed Nov. 18, 2020, and to U.S. Provisional Application No. 63/115,501, filed Nov. 18, 2020, each of which is incorporated by reference in its entirety into this application.

SUMMARY

Briefly summarized, systems and methods disclosed herein are directed to a system for controlling passive flow of a fluid through a drainage tube lumen during a drainage procedure to mitigate the effects of pooling of fluid therein. Dependent loops are formed within drainage tubes when slack portions of tube create a positive incline. These dependent loops trap fluid and can in some instances prevent or restrict flow. In other instances, dependent loops may also cause retrograde flow or reflux (flow toward the patient), leading to various complications. For example, urine pooling within a drainage tube can become a source of catheter associated urinary tract infection ("CAUTI") causing agents such as bacteria, microbes, and the like. Hospital Acquired Infections ("HAI"), such as CAUTI, are detrimental to the patient, and also incur extra costs in treating these additional complications. In some instances, a clinician may connect an air pressure to the drainage tube at a location distal trapped fluid to push the trapped fluid toward and into a fluid collection container. In some instances, a clinician may connect a vacuum source to the drainage tube at a location proximal the trapped fluid to pull the trapped fluid toward and into a fluid collection container. In both instances, since the drainage tube is in fluid communication with the patient, pressures (positive and negative) as applied to the drainage tube may reach the patient resulting in potential complications. As such, isolating the drainage tube from the patient while applying positive and negative pressures to the drainage tube may be advantageous for the patient.

Disclosed herein is a drainage control system including, a tubular body with a tubular body lumen extending from a distal end to a proximal end and a collapsible tube disposed within the tubular body lumen, the collapsible tube including a collapsible tube lumen extending from a distal end to a proximal end of the collapsible tube. In some embodiments, the collapsible tube is attached to the tubular body, such that fluid flow through the tubular body lumen flows through the collapsible tube lumen, and in some embodiments, collapsing the collapsible tube establishes an occlusion of the tubular body lumen preventing fluid flow through the tubular body lumen.

In some embodiments, a circumference of the collapsible tube at the distal end of the collapsible tube is sealably attached to an inside surface of the tubular body, the tubular body comprises an occlusion side port in fluid communication with an outside surface of the collapsible tube, and the occlusion side port is disposed proximal the distal end of the collapsible tube.

In some embodiments, the drainage system includes an occlusion fluid pump coupled to the occlusion side port, such that flow of fluid through the occlusion port exerts a force on the outside surface of the collapsible tube causing the collapsible tube to collapse. In some embodiments, the force is a side force on the collapsible tube that pushes the collapsible tube toward a side of the tubular body lumen. In some embodiments, the fluid is air and the air flow through the occlusion port defines an air jet exiting the occlusion port, producing a dynamic pressure defined by the velocity of the air jet impinging on the collapsible tube.

In some embodiments, a circumference of the collapsible tube at the proximal end and the distal end of the collapsible tube are sealably attached to the inside surface of the tubular body forming an annular chamber between the inside surface of the tubular body and the outside surface of the collapsible tube, and the occlusion side port is in fluid communication with the annular chamber. In some embodiments, fluid flow from the occlusion fluid pump defines a pressure within the annular chamber, and the pressure within the annular chamber exerts an inward force on the outside surface of the collapsible tube causing the collapsible tube to collapse. In some embodiments, the occlusion side port may include a check valve, wherein the check valve permits fluid flow into the annular chamber and prevents fluid flow out of the annular chamber, a relief valve to release pressure from the annular chamber when the relief valve is open, and a porous membrane.

In some embodiments, the drainage system includes a pressure measurement device operatively coupled to the tubular body via a pressure side port disposed distal the distal end of the collapsible tube, and wherein the pressure measurement device is configured to measure the pressure within the tubular body lumen. The pressure port may also include a porous membrane.

In some embodiments, the drainage system includes a controller coupled to the pressure measurement device and the occlusion fluid pump, such that the controller may deactivate the occlusion fluid pump in response to a pressure measurement exceeding a first predefined pressure limit.

In some embodiments, the drainage system includes a purging fluid pump coupled to the tubular body via a purging side port in fluid communication with the tubular body lumen such that fluid flow from the purging pump flows into the tubular body lumen. The purging side port may include a porous membrane. In some embodiments, the controller is coupled to the purging fluid pump, and the controller is configured to deactivate the purging fluid pump in response to a pressure measurement exceeding a predefined pressure limit.

In some embodiments, the tubular body includes a sample side port in fluid communication the tubular body lumen, and the sample side port includes a porous membrane.

In some embodiments, a method of moving fluid through a drainage lumen, includes 1) collapsing the collapsible tube, coupled to the inside surface of a tubular body, to establish an occlusion of the drainage lumen and 2) pumping air into the drainage lumen through a side port of the tubular body proximal the collapsible tube to urge fluid disposed within the drainage lumen in a proximal direction.

In some embodiments, the method includes measuring a pressure inside the lumen at a position distal the occlusion, comparing the measured pressure to a predetermined pressure limit, and discontinuing pumping air into the drainage lumen through a side port if the measured pressure exceeds the predetermined pressure limit.

In some embodiments, the method includes pumping air through a side port into the annular chamber defined by coupling a circumference of the collapsible tube at each end of the collapsible tube to an inside surface of the tubular body to define the annular chamber between an outside surface of the collapsible tube and the inside surface of the tubular body, wherein pumping air into the annular creates a pressure to exert an inward force on the outside surface of the collapsible tube to establish the occlusion. In some embodiments, the method further includes measuring a pressure inside the lumen at a position distal the occlusion, comparing the measured pressure to a predetermined pressure limit, and discontinuing pumping air through the side port if the measured pressure exceeds the predetermined pressure limit.

In some embodiments, the tubular body includes valve that is actuatable between a first configuration and a second configuration. In the first configuration, fluid flow is allowed through the tubular body lumen and in the second configuration, fluid flow is prevented through the tubular body lumen. An airflow source coupled to the valve and pressure from the airflow source actuates the valve from the first configuration to the second configuration. In some embodiments, the valve is biased toward the first configuration such that the valve is disposed in the first configuration in the absence of a pressure from the airflow source. In the second configuration, air from the airflow source flows into the tubular body lumen such that the air flows proximally through the tubular body lumen away from the valve.

In some embodiments, the valve includes a plunger slidably disposed within a valve chamber, and the plunger is positionable between a first position corresponding with the first configuration and a second position corresponding with the second configuration. The plunger includes a lateral lumen extending across the plunger. The lateral lumen defines a portion of the tubular body lumen when the plunger is in the first position. In some embodiments, pressure from the airflow source exerts a force on the plunger toward the second position and a biasing member exerts a force on the plunger toward the first position. The biasing member may be a silicone bellows.

In some embodiments, the drainage system includes a programmable controller coupled to the airflow source, such that the airflow source is activatable by the controller. In some embodiments, the controller is programmed to activate the airflow source at predefined time intervals.

In some embodiments, the drainage system includes a pressure measurement device operatively coupled to the tubular body via a pressure port. The pressure measurement device is also coupled to the controller and the controller is programmed to activate the airflow source in response to a pressure measurement exceeding a predefined pressure limit. In some embodiments, the controller is programmed to deactivate the airflow source in response to a pressure measurement exceeding a predefined pressure limit.

In some embodiments, the drainage system includes a sample port in fluid communication the tubular body lumen, and the sample port includes a porous membrane such that fluid flow through the sample port flows through the porous membrane.

In some embodiments, a method of controlling fluid flow through a drainage lumen, includes providing a valve disposed in line with the drainage lumen. The valve is actuatable between a first configuration and a second configuration in response to a pressure supplied to the valve. In the first configuration, fluid flow is allowed through the drainage lumen and in the second configuration, fluid flow is prevented through the drainage lumen. The method further includes pressurizing the valve to actuate the valve from the first configuration to the second configuration. In some embodiments, the method includes measuring a pressure within the drainage lumen and depressurizing the valve in response to a pressure measurement exceeding a predefined pressure limit.

In some embodiments, a method of removing fluid from a drainage lumen includes providing a valve disposed in line with the drainage lumen. The valve is actuatable between a first configuration and a second configuration in response to an airflow supplied to the valve. In the first configuration, fluid flow is allowed through the drainage lumen and in the second configuration, fluid flow is prevented through the drainage lumen. In the second configuration, airflow is also supplied to the drainage lumen. The method further includes providing airflow to the valve to actuate the valve from the first configuration to the second configuration and to supply airflow to the drainage lumen to remove fluid from the drainage lumen.

In some embodiments, the method of removing fluid from a drainage lumen further includes measuring a pressure within the drainage lumen, and supplying airflow to the valve in response to a pressure measurement exceeding a first predefined pressure limit. The method may further include removing airflow to the valve in response to a pressure measurement exceeding a second predefined pressure limit. In some embodiments, the second predefined pressure limit is greater than the first predefined pressure limit.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
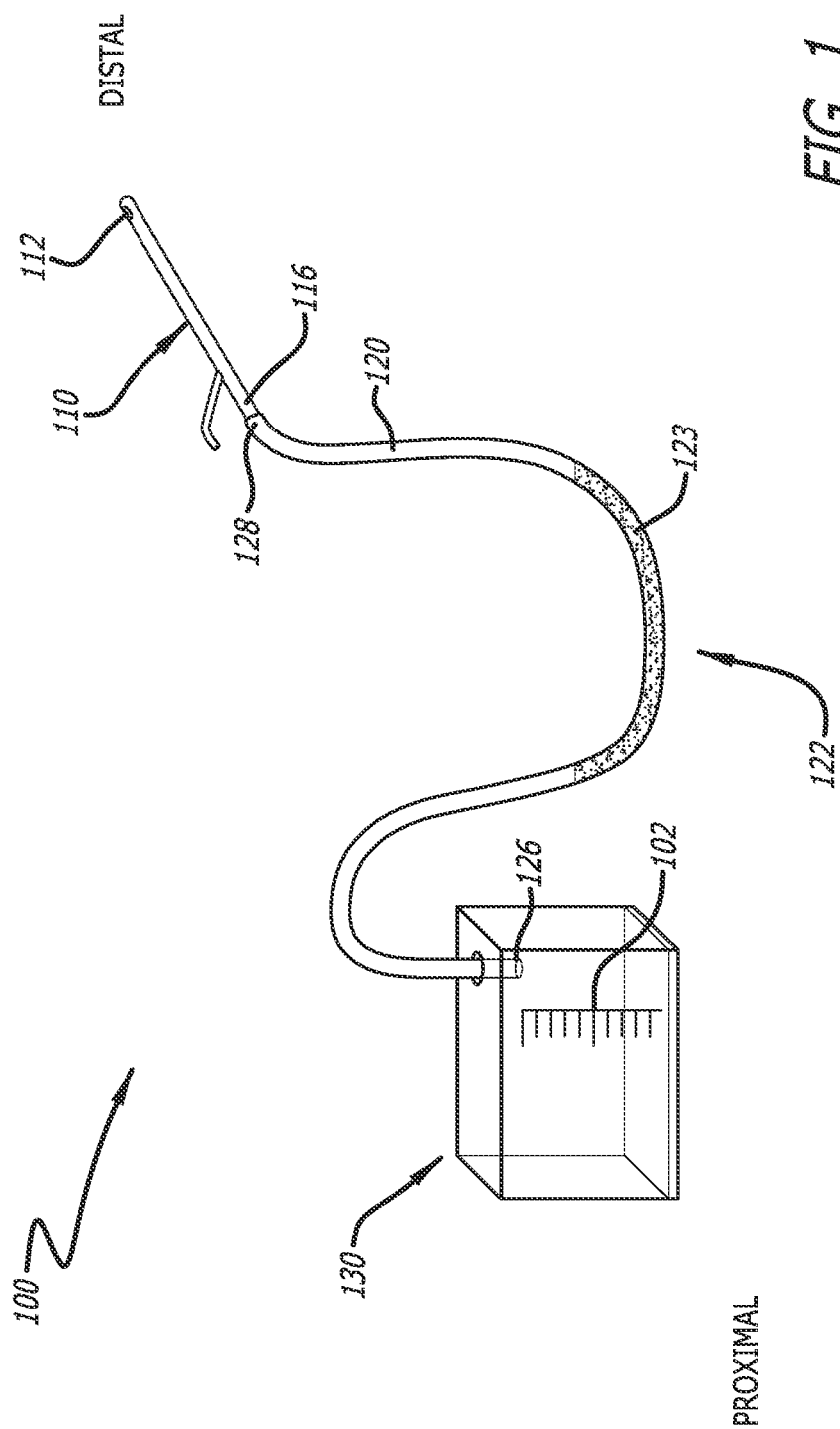
FIG. 1 shows an exemplary catheter and fluid collection system in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

The phrases "connected to" and "coupled to" are broad enough to refer to any suitable coupling or other form of interaction between two or more entities, including mechanical, electrical, fluid, and thermal interaction. Two components may be coupled to each other even though they are not in direct contact with each other. The phrases "attached to" or "attached directly to" refer to interaction between two or more entities which are in direct contact with each other and/or are separated from each other only by a fastener (e.g., adhesives, screws) of any suitable variety. The phrase "fluid communication" refers to arrangements in which a fluid (e.g., a gas or a liquid) can flow from one element to another element when the elements are in fluid communication with each other.

Unless defined otherwise, all technical and scientific terms used herein have the same meaning as commonly understood by those of ordinary skill in the art.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Figure 2A:
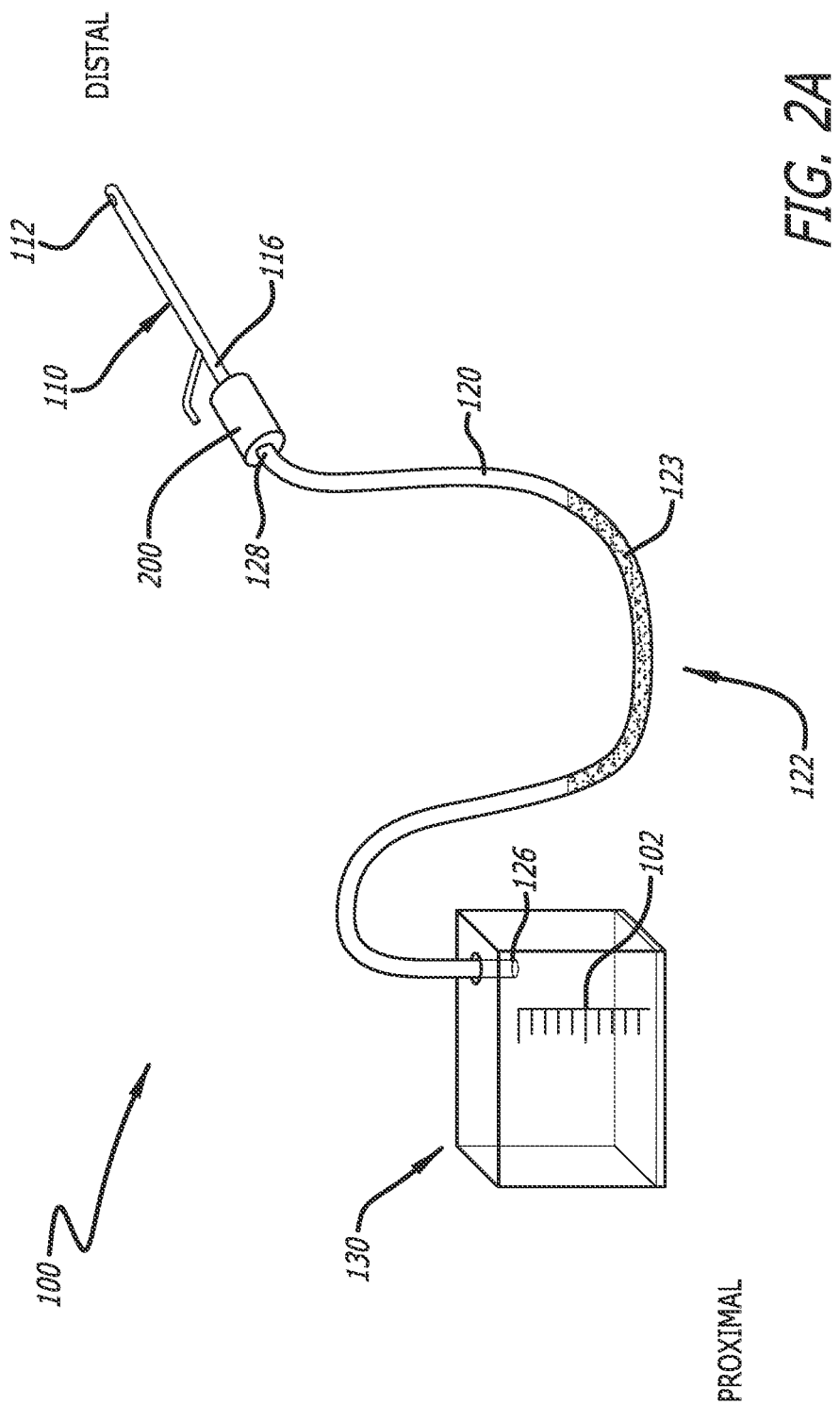
FIG. 2A shows the catheter and fluid collection system of FIG. 1 incorporating a fluid flow control system in accordance with embodiments disclosed herein.

FIGS. 1-2A show an exemplary fluid collection system 100, which generally includes a catheter 110, a drainage tube ("tube") 120 and a collection container ("container") 130. FIG. 2A shows an exemplary fluid collection system 100 further including a fluid flow control system (FFCS) 200. Exemplary catheters 110 include indwelling catheters, Foley catheters, balloon catheters, peritoneal drainage catheters, or the like, and are configured to be inserted into an orifice within the body of a patient to drain a fluid 123 therefrom. In an embodiment, the catheter 110 can be inserted through the urethra and into a bladder of a patient. The catheter 110 includes an eyelet 112 that provides fluid communication with a lumen of the catheter 110, and is configured to drain the fluid 123, e.g., urine.

The tube 120 extends from a distal end 128 to a proximal end 126 to define an axial length, and defines a lumen. In the illustrated embodiment, the distal end 128 of the tube 120 is configured to engage a proximal end 116 of the catheter 110. The tube 120 provides fluid communication between the lumen of the catheter 110 and the collection container 130. The tube 120 can be formed of rubber, plastic, polymer, silicone, or similar suitably compliant material. The collection container 130 can include a rigid container, a flexible collection bag, or similar suitable container for receiving a fluid 123, e.g. urine, drained from the catheter 110. In an embodiment, the container 130 includes graduated markings 102 for measuring a fluid disposed therein. FIG. 1 shows a dependent loop 122. The dependent loop 122 may be any portion of the tube 120 that is lower than a downstream portion so as to create a positive incline relative to the direction of fluid flow. Dependent loops 122 can form in slack portions of the tube 120. The dependent loop 122 may be a complete loop, a partial loop, or any segment of tubing 120 that causes fluid 123 to pool in the tubing 120. In use, one or multiple dependent loops 122 can form along the length of the tube 120. In some instances, pooling of the fluid 123 within the tube 120 can be detrimental to the patient.

FIG. 2A shows the fluid collection system 100 incorporating a fluid flow control system (FFCS) 200. The FFCS 200 is connected in line with the fluid collection system 100 such that the FFCS 200 forms a portion of the lumen of the fluid collection system 100. In other words, fluid 123 flows through the lumen also flows through the FFCS 200. In some embodiments, the FFCS 200 may be connected between the catheter 110 and tube 120.

Figure 2B:
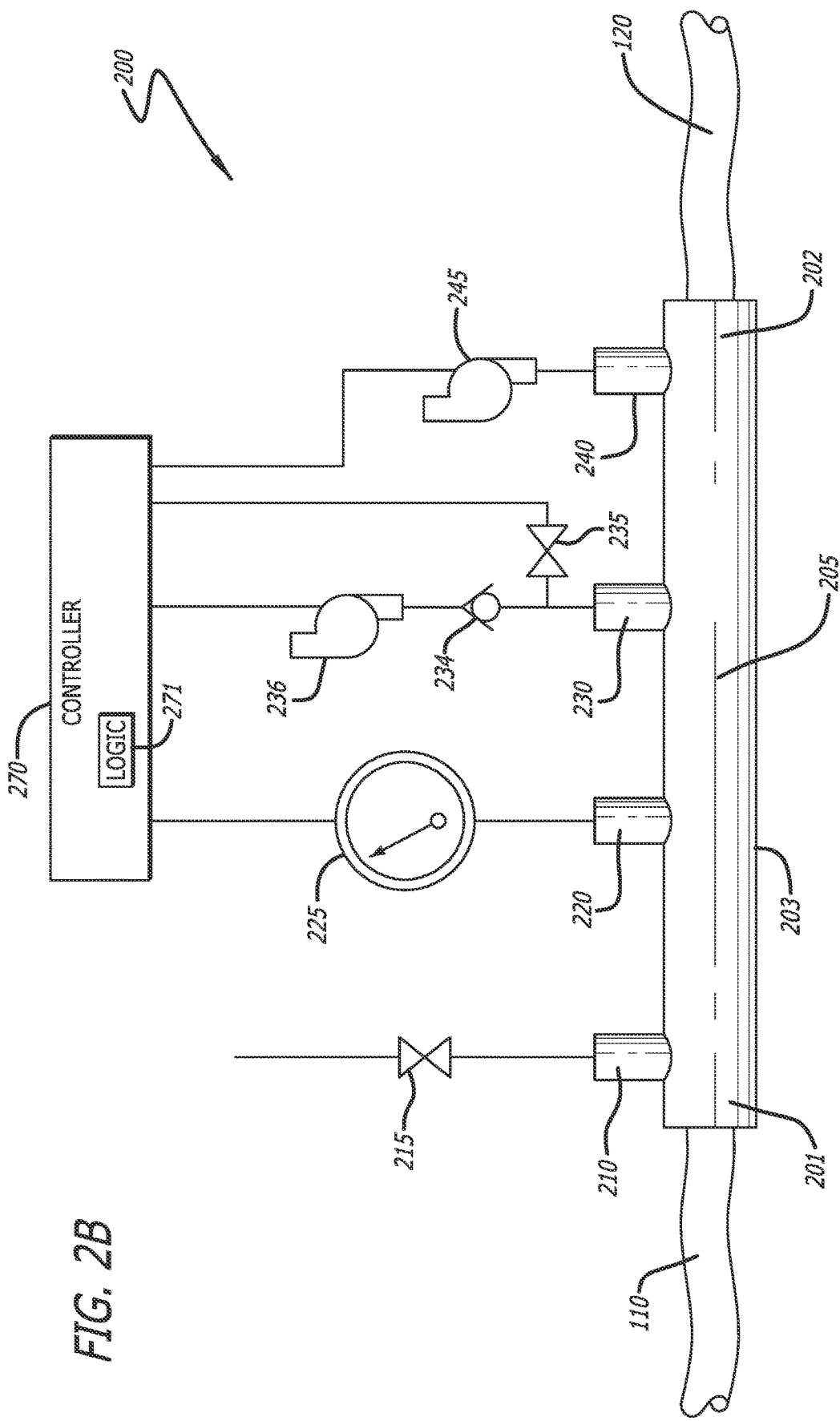
FIG. 2B is an illustration of a fluid flow control system in accordance with embodiments disclosed herein.
Figure 3:
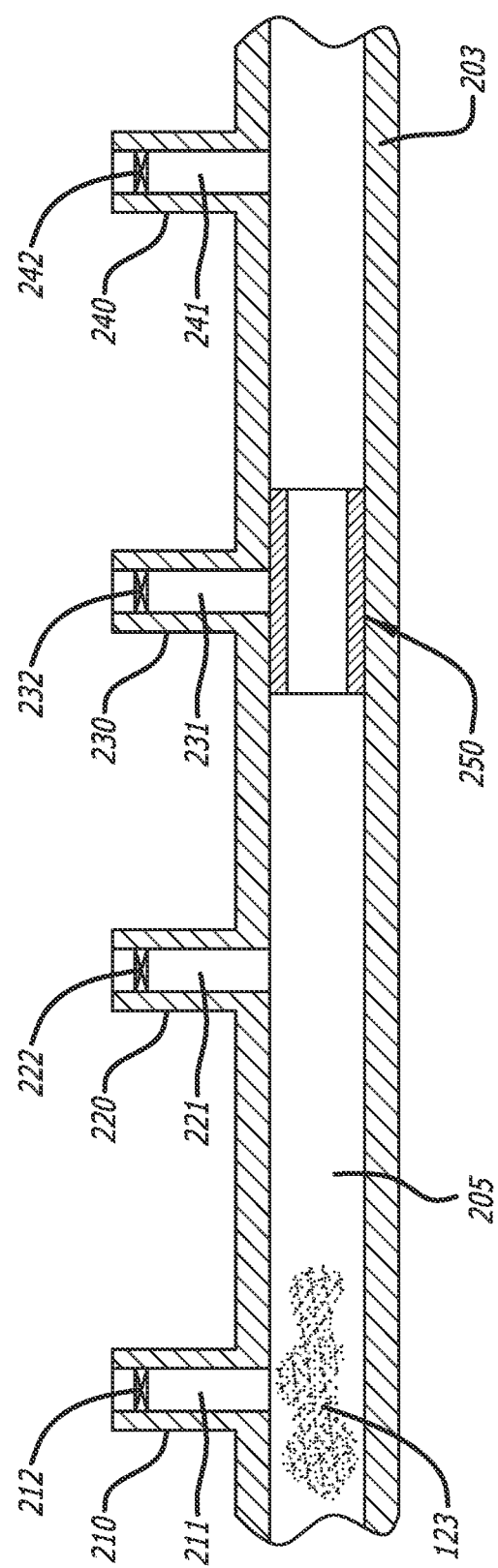
FIG. 3 is a cross-sectional view of a portion of the fluid flow control system in accordance with embodiments disclosed herein.

Reference is now made to FIGS. 2B-3, wherein FIG. 2B illustrates a fluid flow control system (FFCS) 200 and FIG. 3 is a cross-sectional view of a portion of the FFCS 200. The FFCS 200 may provide for multiple functionalities related to the fluid 123 within a main flow lumen 205 of the FFCS 200, including sampling of the fluid 123, sensing pressure of the fluid 123, controlling flow of the fluid 123, and purging fluid 123 from the tube 120. Each of these functionalities are further described below.

The FFCS 200 includes a tubular body 203 defining main flow lumen 205 extending from the distal end 201 to the proximal end 202. The tubular body 203 may comprise connection features at the distal and proximal ends 201, 202 to facilitate attaching of the tubular body 203 to the catheter 110 and tube 120. The tubular body 203 may also include multiple side ports as further described below. The tubular body 203 may be formed of thermoplastic material such a polycarbonate, nylon, polypropylene or any other suitable thermoplastic material and may be injection molded. The tubular body 203 may be a single component or formed of multiple components coupled together.

The tubular body 203 may include a sample port 210 to facilitate obtaining a sample of the fluid 123. The sample port 210 includes a sample port lumen 211 in fluid communication with the main flow lumen 205. The sample port 210 may be configured to couple to medical fluid handling components such as tubing, connectors, stopcocks, and syringes. In some embodiments, the sampling port may include coupling features consistent with a medical connection standard such as a female Luer standard.

The sample port 210 may include a sample port vent 212. The sample port vent 212 may be coupled to the sample port 210 such that fluid passing through the sample port lumen 211 passes through the sample port vent 212. The sample port vent 212 may be positioned at an open end of the sample port 210 or disposed within the sample port lumen 211. The sample port vent 212 may be a porous membrane formed of a sintered polytetrafluoroethylene (PTFE), an acrylic copolymer with a nylon backing, or any suitable materials or structures. In some embodiments, the sample port vent 212 may be hydrophilic so as to freely allow passage of a liquid. In other embodiments, the sample port vent 212 may be hydrophobic so as to inhibit passage of a liquid in the absence a pressure sufficient to cause liquid to break through the membrane. A hydrophobic membrane may facilitate prevention of liquid passage through the sample port lumen 211 except for when a medical practitioner is actively obtaining a sample. A pore size of the sample port vent 212 may be varied to optimize a breakthrough pressure. The sample port vent 212 may be attached to the sample port 210 via any suitable attachment method such as ultrasonic welding, heat staking, and adhesive gluing, for example.

In some embodiments, the sample port 210 may include a manually operated sampling valve 215. The valve 215 may be a separate device coupled to the sampling port 210 such as a stopcock or the sampling valve 215 may be formed integral to the sample port 210. The valve 215 may provide for selective opening and closing of the sample port lumen 211. For example, in some instances, the sampling valve 215 may generally remain closed during the drainage process and opened when a sample of fluid 123 is obtained.

The tubular body 203 may include a pressure port 220 to facilitate measuring the pressure of the fluid 123 within the main flow lumen 205. The pressure port 220 may include a pressure port lumen 221 in fluid communication with the main flow lumen 205. In the illustrated embodiment, the sample port 210 may be disposed distal the pressure port 220. In other embodiments, the sample port 210 may be disposed proximal the pressure port 220. In some instances, an abnormal pressure within the catheter may be indicative of potential patient complications. As such, measuring the pressure and taking steps to resolve an abnormal pressure condition may prevent patient complications. In a similar fashion to the sample port 210, the pressure port 220 may be coupled to a pressure measurement device 225. In some embodiments, the pressure measurement device 225 may be in fluid communication with the main flow lumen 205 via a second fluid. In other words, the second fluid (e.g., air) may be disposed between the pressure measurement device 225 and the fluid 123 so that the fluid 123 does not directly contact the pressure measurement device 225. In some embodiments, the fluid 123 may be separated from the pressure measurement device 225 via a flexible member such as a diaphragm. In such embodiments, pressure of the fluid 123 may push on the diaphragm which in turn may push on a pressure transducer to facilitate a pressure measurement.

The pressure port 220 may include a pressure port vent 222. The pressure port vent 222 may be coupled to the pressure port 220 such that fluid passing through the pressure port lumen 221 passes through the pressure port vent 222. The pressure port vent 222 may be positioned at an open end of the pressure port 220 or disposed within the pressure port lumen 221. The pressure port vent 222 may be a porous membrane formed of a sintered PTFE, an acrylic copolymer with a nylon backing, or any suitable materials or structures. In some embodiments, the pressure port vent 222 may be hydrophilic so as to freely allow passage of a liquid. In other embodiments, the pressure port vent 222 may be hydrophobic so as to inhibit passage of a liquid during use. A hydrophobic membrane may help prevent the liquid 123 from contact a pressure transducer. The pressure port vent 222 may be attached to the pressure port 220 via any suitable attachment method such as ultrasonic welding, heat staking, and adhesive gluing, for example.

The FFCS 200 may include a pressure measurement device 225 operatively coupled to the pressure port 220. The pressure measurement device 225 may include a pressure transducer fluidly coupled to the main fluid lumen 205 via the pressure port 220 so that the pressure measurement device 225 can provide a pressure measurement of the fluid 123 within the main flow lumen 205 at the location of the pressure port 220. The pressure measurement device 225 may be configured to provide a visual indication of the measured pressure. The pressure measurement device 225 may be configured to provide audible indication of the measured pressure such as an alarm if the measured pressure exceeds one or more predetermined limits. The pressure measurement device 225 may also be coupled to a controller 270 as described below.

The tubular body 203 includes an occlusion port 230 having an occlusion port lumen 231. The occlusion port 230 may be disposed proximal to the pressure port 220. The occlusion port 230 is in fluid communication with an occlusion mechanism 250, which will be described in detail below. The occlusion port 230 may include an occlusion port vent 232. The occlusion port vent 232 may be coupled to the occlusion port 230 such that fluid passing through the occlusion port lumen 231 passes through the occlusion port vent 232. The occlusion port vent 232 may be positioned at an open end of the occlusion port 230 or disposed within the occlusion port lumen 231. The occlusion port vent 232 may be a porous membrane formed of a sintered PTFE, an acrylic copolymer with a nylon backing, or any suitable materials or structures. In some embodiments, the occlusion port vent 232 may be hydrophilic so as to freely allow passage of a liquid or a gas. In other embodiments, the occlusion port vent 232 may be hydrophobic so as to inhibit passage of a liquid during use. A hydrophobic membrane may help prevent the liquid 123 from flowing through the occlusion port lumen 231 during use. The occlusion port vent 232 may be attached to the occlusion port 230 via any suitable attachment method such as ultrasonic welding, heat staking, and adhesive gluing, for example.

In an embodiment, the occlusion port 230 may be coupled to an occlusion pump 236. The occlusion pump 236 can be a mechanical pump, syringe, squeeze bulb, or similar device for providing a pressurized operating fluid. The operating fluid may be a gas such as air or a liquid such as water. The occlusion pump 236 may be a source of compressed gas, such as a compressed gas bottle, medical compressed air line, or the like. The occlusion pump 236 can provide a pressurized fluid for selectively activating the occlusion mechanism 250. In some embodiments, the occlusion pump 236 may also provide a vacuum for selectively deactivating the occlusion mechanism 250. As further described below, activating the occlusion mechanism 250 may prevent flow of fluid 123 through the main flow lumen 205, and deactivating the occlusion mechanism 250 may restore flow through the main flow lumen 205.

In some embodiments, the occlusion port 230 may include a check valve 234 in-line with the occlusion port lumen 231. The check valve 234 may be oriented so as allow fluid flow from the occlusion pump 236 toward the occlusion mechanism 250 and prevent flow from the occlusion mechanism 250 toward the occlusion pump 236. As such, the occlusion mechanism 250 may remain activated (pressurized) when the occlusion pump 236 is deactivated (turned off). The check valve 234 may be a separate part coupled to the occlusion port 230 or may be formed integral to the occlusion port 230.

In some embodiments, the occlusion port 230 may further include a relief valve 235 in fluid communication with the occlusion port lumen 231 at a location between the check valve 234 and the occlusion mechanism 250. The relief valve 235 may be configured to release pressure from the occlusion mechanism 250 and thereby deactivate the occlusion mechanism 250. In some embodiments, the relief valve 235 may be 1) a two-way stopcock with one leg in fluid communication with the occlusion port lumen 231, 2) a push button device that, when pushed, vents pressure from the occlusion port lumen 231, or 3) a mechanism that defeats the checking function of the check valve 234. As may be appreciated by one of ordinary skill, the relief valve 235 may be any devise or mechanism that selectively prevents and allows fluid flow out of the occlusion mechanism 250. The relief valve 235 may expel released fluid directly to the atmosphere or back to the occlusion port lumen 231 at a point between the check valve 234 and the occlusion pump 236. As with the check valve 234, the relief valve 235 may be a separate part coupled to the occlusion port 230 or may be formed integral to the occlusion port 230. In some embodiments, the relief valve 235 may be a controllable electro-mechanical valve.

The tubular body 203 may include a purging port 240. The purging port 240 may facilitate the introduction of fluid (e.g., air) into the tube 120 at a point proximal the occlusion port 230. The introduction of air may purge fluid 123 from the tube 120 such as fluid 123 pooled in a dependent loop. The purging port 240 may be coupled to a purging pump 245. The purging pump 245 may be a source of compressed gas, such as a compressed gas bottle, medical compressed air line, or the like. In an embodiment, the purging pump 245 can be triggered automatically using sensors, by a time-based trigger, an action-based trigger, or combinations thereof, to start/stop the purging process. In use, the main flow lumen 205 may be occluded by the occlusion mechanism 250 prior to initiating the purging pump 245 so as to prevent flow of the fluid 123 toward the patient (retrograde flow) and to prevent pressure from the purging pump 245 from reaching the patient.

The purging port 240 may include a purging port vent 242. The purging port vent 242 may be coupled to the purging port 240 such that fluid passing through the purging port lumen 241 passes through the purging port vent 242. The purging port vent 242 may be positioned at an open end of the purging port 240 or disposed within the purging port lumen 241. The purging port vent 242 may be a porous membrane formed of a sintered PTFE, an acrylic copolymer with a nylon backing, or any suitable materials or structures. In other embodiments, the purging port vent 242 may be hydrophobic so as to inhibit passage of a liquid during use. A hydrophobic membrane may help prevent the liquid 123 from flowing toward the purging pump 245. The purging port vent 242 may be attached to the purging port 240 via any suitable attachment method such as ultrasonic welding, heat staking, and adhesive gluing, for example.

Figure 4A:
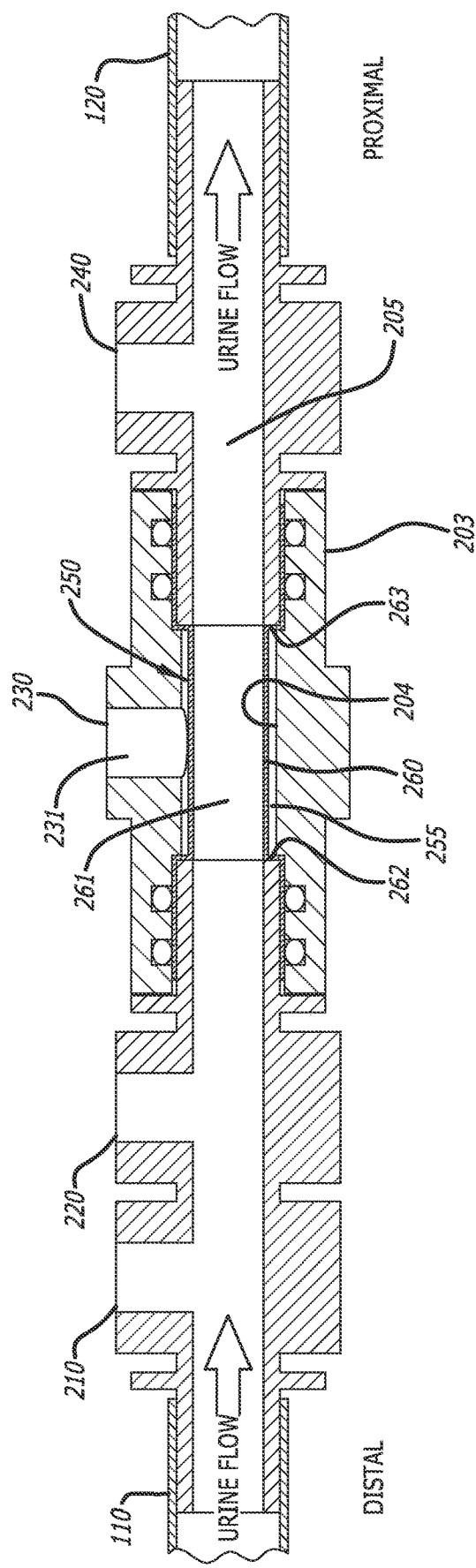
FIG. 4A is a detail cross-sectional view of an occlusion mechanism of the fluid flow system control system of FIG. 3 with the occlusion mechanism disposed in a non-occluded state in accordance with embodiments disclosed herein.
Figure 4B:
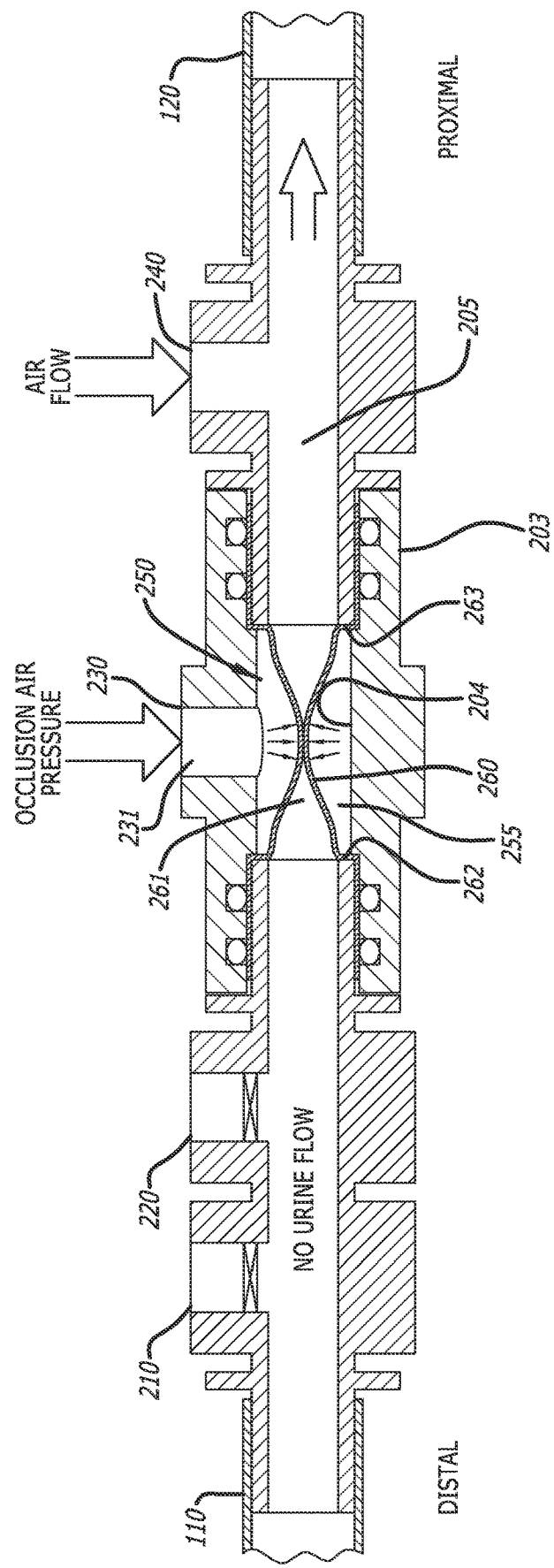
FIG. 4B is a detail cross-sectional view of the occlusion mechanism of the fluid flow control system of FIG. 3 with the occlusion mechanism disposed in an occluded state in accordance with embodiments disclosed herein.

FIGS. 4A and 4B show cross-sectional detail views of a portion of the tubular body 203 including the occlusion mechanism 250. FIG. 4A illustrates the occlusion mechanism 250 in a non-occluded state and 4B illustrates the occlusion mechanism 250 in an occluded state. The occlusion mechanism 250 includes a collapsible tube 260 and an annular chamber 255. The collapsible tube 260 is disposed within the main flow lumen 205 of the tubular body 203. The collapsible tube 260 forms a collapsible lumen 261 extending from a distal end 262 and to a proximal end 263. The collapsible tube 260 is attached to the tubular body 203 at each of the distal end 262 and the proximal end 263. An entire circumference at each of the distal end 262 and the proximal end 263 is sealably attached to an inside surface 204 of tubular body 203 such that the collapsible lumen 261 forms a segment of the main flow lumen 205. In other words, flow of the liquid 123 through the main flow lumen 205 also flows through the collapsible lumen 261. At least a portion of the collapsible tube 260 between the distal end 262 and the proximal end 263 is not attached to the inside surface 204 and thus is free to move away from the inside surface 204. The collapsible tube 260 may be attached to the tubular body 203 via any suitable attachment method such as ultrasonic welding, heat staking, and adhesive gluing, for example. The collapsible tube 260 may also be clamped or secured between mating components of the tubular body 203.

The annular chamber 255 is defined by an outside surface of the collapsible tube 260, the inside surface 204, the distal end 262, and the proximal end 263. The attachment of the distal end 262 of the collapsible tube 260 to the inside surface 204 defines a closed distal end of the annular chamber 255. Similarly, the attachment of the proximal end 263 to the inside surface 204 defines a closed proximal end of the annular chamber 255. The annular chamber 255 is fluidly isolated from the main flow lumen 205 such that there is no fluid communication between the annular chamber 255 and main flow lumen 205. As such, fluid from the occlusion pump 236 does not enter the main flow lumen 205. The occlusion port lumen 231 is in fluid communication with the annular chamber 255. In operation, displacement of the operating fluid through the occlusion port lumen 231 and into the annular chamber 255 displaces at least a portion of the collapsible tube 260 inward away from the inside surface 204 effectively reducing a flow area of the collapsible tube lumen 261. Said another way, a pressure within the annular chamber 255, as defined by the occlusion pump 236, exerts an inward force on the collapsible tube 260 causing the collapsible tube 260 to collapse and occlude the collapsible lumen 261 as illustrated in FIG. 4B. In some instances, the collapsible tube 260 may be partially collapsed so as to partially occlude the collapsible lumen 261, thereby controlling a flow rate of the fluid 123 through the fluid collection system 100.

The collapsible tube 260 may include various materials, features, and forms. The collapsible tube 260 may be formed of elastomeric or flexible plastics or rubbers, including silicone, latex, polyvinyl chloride, polyethylene, low-density polyethylene, and polypropylene. The collapsible tube 260 may be constructed of a thin wall. The collapsible tube 260 may be a section of an extruded tube or a molded preform. The collapsible tube 260 may have a consistent cross-sectional shape along its length or a varying cross-sectional shape. The collapsible tube 260 may comprise portions of varying thickness so as to establish varying flexibility properties along a length and/or around a circumference of the collapsible tube 260. For example, the collapsible tube 260 may include sections of lower flexibility (increased stiffness) near the distal and proximal ends 262, 263 and a section of greater flexibility (decreased stiffness) along a middle section. The greater stiffness at the ends may facilitate attachment to the inside surface 204. The collapsible tube 260 may also include longitudinal ribs, folds, or other forms of stiffness variation around a circumference which may induce the collapsible tube 260 to assume a predefined cross-sectional shape when collapsed.

In an embodiment, the FFCS 200 may include a controller 270. The controller 270 may include a microprocessor, memory, and an interface comprising one or more digital/analog inputs and outputs. The controller 270 may be be configured to receive an input and provide an output control signal and may be further configured to continually monitor an input signal and compare the input signal with one or more programmed limits as stored in memory. In some embodiments, the controller 270 may be a microcontroller, i.e., a small computer on a single integrated circuit comprising one or more CPUs (processor cores) along with memory and programmable input/output peripherals.

The controller 270 may be electrically coupled to one or more of the occlusion pump 236, the relief valve 235, and the purging pump 245. The controller 270 may include controller logic 271 that controls the operation of the occlusion pump 236, the relief valve 235, and the purging pump 245. In some embodiments, the controller 270 may be a programmable controller configured to detect failures of the occlusion mechanism 250 and initiate a response to prevent a pressure increase in the main flow lumen 205 from reaching the patient. For example, a failure of the annular chamber 255 may allow the operating fluid from the occlusion pump 236 to enter the main flow lumen 205 which may in some instances cause an increased pressure in the catheter 110 resulting potential patient complications. In such an instance, the controller 270 may compare the measured pressure to a predetermined pressure limit. If the measured pressure exceeds the predetermined limit, the controller 270 may deactivate the occlusion pump 236 and/or activate (open) the relief valve 235, thereby keeping the patent safe from increased pressure.

By way of another example, a failure of the occlusion mechanism 250 to occlude the main flow lumen 205 may allow air from the purging pump 245 to pass distally through the occlusion mechanism 250 and enter the catheter 110 which may in some instances cause an increased pressure in the catheter 110. In this instance, the controller 270 may compare the measured pressure to the predetermined pressure limit. If the measured pressure exceeds the predetermined limit, the controller 270 may deactivate the purging pump 245, thereby keeping the patent safe from the increased pressure. In this instance, the controller may also deactivate the occlusion pump 236 and/or activate (open) the relief valve 235.

Use of the FFCS 200 may include one or more of the following steps, methods or processes. A fluid collection system may be assembled by attaching a catheter to the distal end of the FFCS 200 and a drainage tube to the proximal end thereby establishing a continuous drainage flow path. A medical practitioner may connect the drainage assembly to a patient and establish a flow of drainage fluid into a fluid collection container. The medical practitioner may connect a sampling device, such as a syringe, to the sample port of the FFCS and withdraw a sample of drainage fluid. The medical practitioner may connect an occlusion pump to the occlusion port and activate the occlusion pump to activate an occlusion mechanism of the flow path through the FFCS. The medical practitioner may deactivate the occlusion pump, thereby removing the occlusion from the flow path through the FFCS. The medical practitioner may couple a pressure measurement device to the pressure port of the FFCS to monitor pressure within the flow path. The medical practitioner may configure the pressure measurement device to provide an audio and/or visual indication if the pressure exceeds one or more limits. The medical practitioner may connect a purging pump to the purging port. The medical practitioner may activate the purging pump to purge drainage fluid from the drainage tube after establishing a pressure to the occlusion port. The medical practitioner may couple a programmable controller to the pressure measurement device and the purging pump so that the purging pump may be automatically defeated by a signal from the pressure measurement device. In such an instance, the pressure measurement device may detect a failure of the occlusion mechanism (a non-occluded flow path) and deactivate the purging pump, thereby preventing increased pressure from affecting the patient. After purging fluid from the drainage tube, the medical practitioner may deactivate the purging pump and thereafter, deactivate the occlusion pump.

Figure 5:
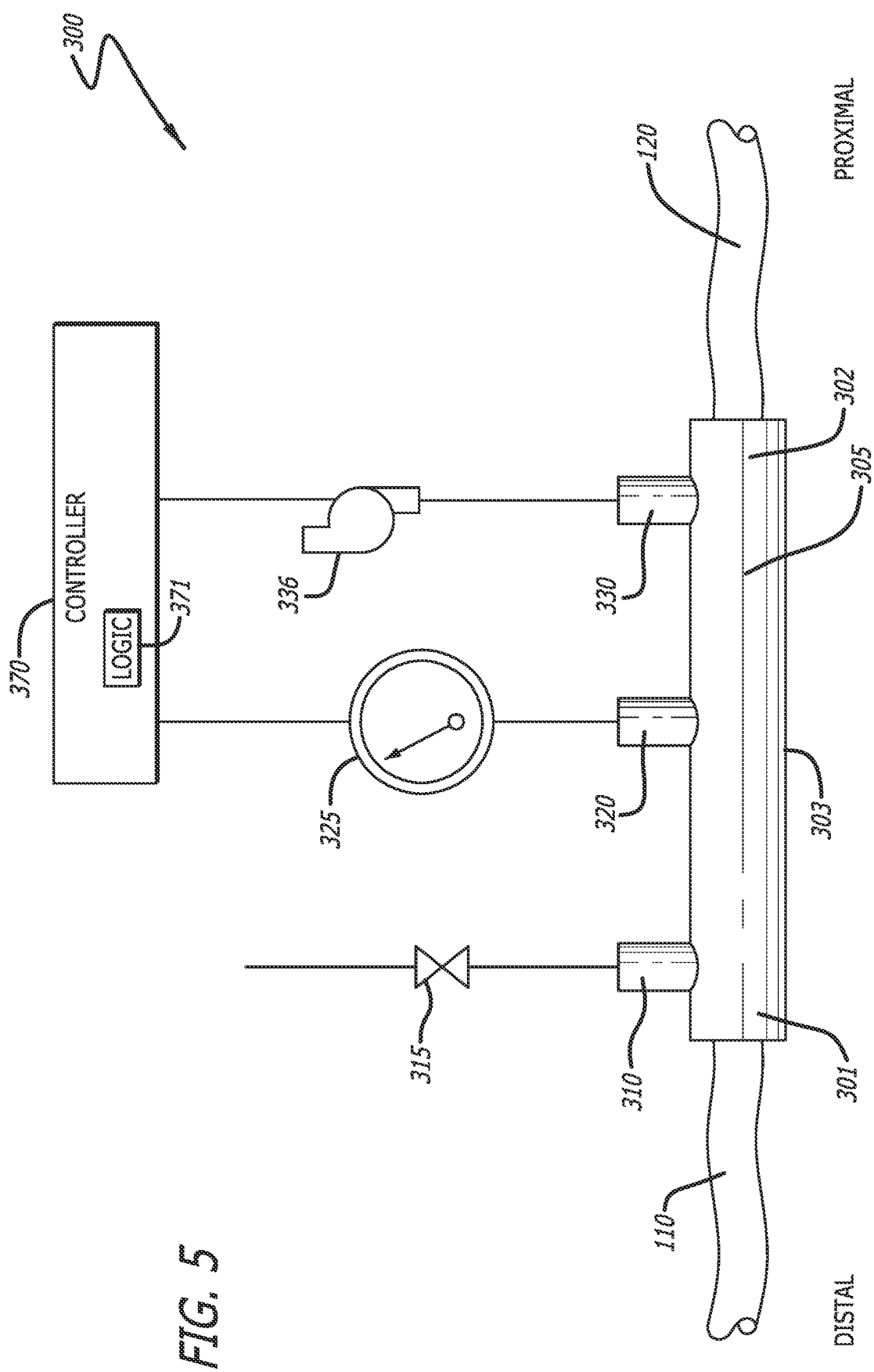
FIG. 5 is an illustration of a fluid flow control system in accordance with embodiments disclosed herein in accordance with embodiments disclosed herein.
Figure 6A:
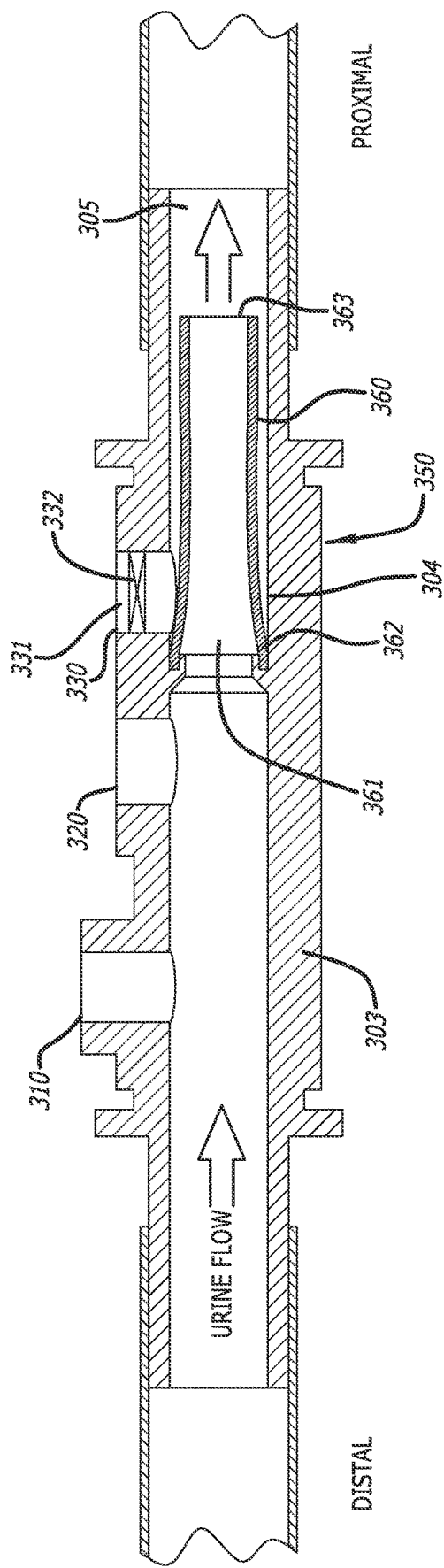
FIG. 6A is a detail cross sectional view of a portion of the fluid flow control system of FIG. 5 with the occlusion mechanism disposed in a non-occluded state in accordance with embodiments disclosed herein.
Figure 6B:
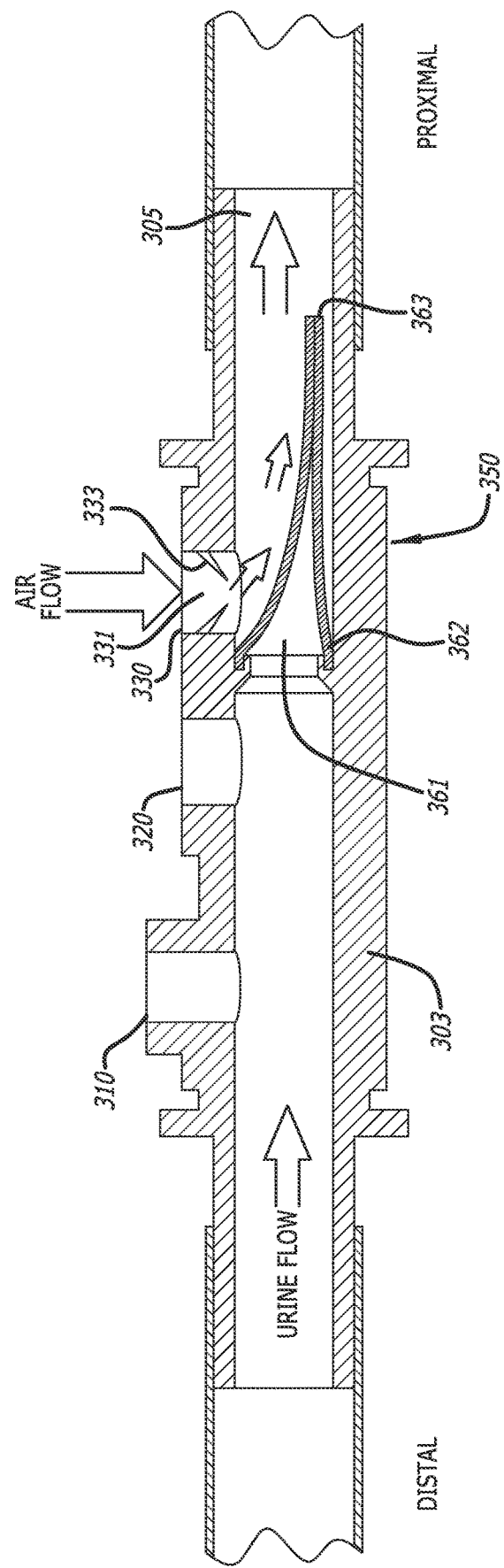
FIG. 6B is a detail cross sectional view of a portion of the fluid flow control system of FIG. 5 with the occlusion mechanism disposed in an occluded state in accordance with embodiments disclosed herein.

FIGS. 5-6B illustrate a fluid flow control system (FFCS) 300 that can, in certain respects, resemble components of the FFCS 200 described in connection with FIGS. 2-4B. It will be appreciated that all the illustrated embodiments may have analogous features. Accordingly, like features are designated with like reference numerals, with the leading digits incremented to "3." For instance, the body is designated as "203" in FIGS. 1A-4B, and an analogous body is designated as "303" in FIGS. 5-6B. Relevant disclosure set forth above regarding similarly identified features thus may not be repeated hereafter. Moreover, specific features of the FFCS 200 and related components shown in FIGS. 2-4B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the FFCS of FIGS. 5-6B. Any suitable combination of the features, and variations of the same, described with respect to the FFCS 200 illustrated in FIGS. 2-4B can be employed with the FFCS 300 of FIGS. 5-6B, and vice versa.

The FFCS 300 includes a tubular body 303 defining main flow lumen 305 extending from the distal end 301 to the proximal end 302. The tubular body 303 may comprise connection features at the distal and proximal ends 301, 302 to facilitate attaching the tubular body 303 to the catheter 110 and tube 120. The FFCS 300 may include a sample port 310, pressure port 320, a pressure measurement device 325 that may comprise similar components and functionality as the sample port 210, the pressure port 220 and the pressure measurement device 225 described above in relation to the FFCS 200.

The tubular body 303 includes an occlusion port 330 having an occlusion port lumen 331. The occlusion port 303 is disposed proximal the pressure port 320. The occlusion port lumen 331 is in fluid communication with an occlusion mechanism 350 and the main flow lumen 305. The occlusion port 330 may be coupled to an occlusion pump 336 so that the occlusion pump 336 is operatively coupled the occlusion mechanism 350. The occlusion pump 336 may be a source of compressed gas, such as a compressed gas bottle, medical compressed air line, or the like. The occlusion pump 336 can provide a flow of fluid for activating the occlusion mechanism 350. In an embodiment, the occlusion pump 336 can be triggered automatically using sensors, by a time-based trigger, an action-based trigger, or combinations thereof, to selectively activate/deactivate the occlusion mechanism 350. In the illustrated embodiment, the occlusion pump 336 may provide a flow of air. As further described below, air flow through the occlusion port 330 may activate the occlusion mechanism 350 and thereby occlude the main flow lumen 305. Discontinuing the air flow (turning off the occlusion pump 336) may deactivate the occlusion mechanism 350 and thereby restore flow of the fluid 123 through the main flow lumen 305.

The occlusion port 330 may form a nozzle 333 at the inward end of the occlusion port 330, i.e., the end of the occlusion port 300 adjacent the main flow lumen 305. The nozzle 333 may define a size of the occlusion port lumen 331, that increases the velocity of air exiting the occlusion port lumen 331 to form an air jet. The nozzle 333 may also define a cross-sectional shape of the air jet. In some embodiments, the cross-sectional shape may be round, oval, or flat. The shape of the air jet may facilitate a reliable occlusion of the collapsible tube 360. The occlusion port 330 may include an occlusion port vent 332 that may comprise similar components and functionality as the occlusion port vent 232 of FFCS 200.

FIGS. 6A and 6B show cross-sectional detail views of a portion of the tubular body 303 including the occlusion mechanism 350. FIG. 6A illustrates the occlusion mechanism 350 in a non-occluded state and FIG. 6B illustrates the occlusion mechanism 350 in an occluded state. The occlusion mechanism 350 includes a collapsible tube 360 disposed within the main flow lumen 305. The collapsible tube 360 forms a collapsible lumen 361 extending from a distal end 362 and to a proximal end 363. The collapsible tube 360 is attached to the tubular body 303 at the distal end 362 of the collapsible tube 360. An entire circumference of the collapsible tube 360 at the distal end 362 is sealably attached to an inside surface 304 of the tubular body 303 such that the collapsible lumen 361 forms a segment of the main flow lumen 305. In other words, the liquid 123 flows through the collapsible lumen 361 entering at the distal end 362. At least a portion of the collapsible tube 360 extending away from the distal end 362 including the proximal end 363 is not attached to the inside surface 304 and is free to move away from the inside surface 304.

In operation, air flow from the occlusion pump 336 passes through the occlusion port lumen 331 forming the air jet directed toward a side of the collapsible tube 360. As the air jet impinges on the side of a collapsible tube, a dynamic pressure is generated that is proportional to the square of the air jet velocity. The dynamic pressure exerts a side force on the collapsible tube 360 urging a portion of the collapsible tube 360 toward a side of the main flow lumen 305 opposite the occlusion port 330 as shown in FIG. 6B. The dynamic pressure causes the collapsible tube 360 to collapse along the inside surface 304 of the main flow lumen 305 opposite the occlusion port 330. As the flow of the fluid 123 passes through the collapsible tube lumen 361, the flow of the fluid 123 is stopped when the collapsible tube 360 is collapsed. Flow of the fluid 123 is restored when the occlusion pump 336 is deactivated because the dynamic pressure exerted on the collapsible tube 360 is eliminated.

The collapsible tube 360 may include various materials, features, and forms. The collapsible tube 360 may be formed of elastomeric or flexible plastics or rubbers, including silicone, latex, polyvinyl chloride, polyethylene, low-density polyethylene, and polypropylene. The collapsible tube 360 may be a section of an extruded tube or a molded preform. The collapsible tube 360 may have a consistent cross-sectional shape along its length or a varying cross-sectional shape, such as a conical shape, for example. In some embodiments, the collapsible tube 360 may comprise portions of varying thickness so as to establish varying flexibility properties. For example, the collapsible tube 203 may include sections of lower flexibility (increased stiffness) near the distal end 362, and a section of greater flexibility (decreased stiffness) toward the proximal end 363. The increased stiffness at the distal end 362 may facilitate attachment to the inside surface 304 and the decreased stiffness as the proximal end 363 may facilitate collapsibility. The collapsible tube 360 may also include longitudinal ribs, folds, or other forms of stiffness variation along a length and around a circumference of the collapsible tube 360 which may induce the collapsible tube 360 to assume a predefined cross-sectional shape when collapsed, such as a flat shape, for example.

The air flow from the occlusion pump 336 passes through the occlusion port lumen 331 and into the main flow lumen 305. Since the collapsible tube 360 is occluded by the dynamic pressure of the air flow, the air flow is prevented from traveling in a distal direction (toward the patient) through the main flow lumen 305. As such, the air flow travels in a proximal direction through the main flow lumen 305 and continues proximally through the tube 120, thereby purging fluid 123 from the tube 120 such as fluid 123 pooled in a dependent loop 122. In this way, the flow of air provided by the occlusion pump 336 may occlude of the main flow lumen 305 and purge fluid 123 from the tube 120 in a single step.

In an embodiment, the controller 370 can, in certain respects, resemble components of the controller 270 described in connection with FIGS. 5-6B. The controller 370 may be electrically coupled to the pressure measurement device 325 and the occlusion pump 336. The controller 370 may include logic 371 that controls the operation of the occlusion pump 336.

In some embodiments, the controller 370 may be a programmable controller configured to detect failures of the occlusion mechanism 350 and initiate a response to prevent a pressure increase in the main flow lumen 305 from reaching the patient. For example, a failure of the occlusion mechanism 350 to occlude the main flow lumen 305 may allow air from the occlusion pump 336 to flow distally into the catheter 110 which may in some instances cause an increased pressure in the catheter 110. In this instance, the controller 370 may compare the measured pressure to a predetermined pressure limit. If the measured pressure exceeds the predetermined limit, the controller 370 may deactivate the occlusion pump 336, thereby eliminating the increased pressure and keeping the patent safe.

Use of the FFCS 300 may include one or more of the following steps, methods or processes. A fluid collection system may be assembled by attaching a catheter to the distal end of the FFCS and a drainage tube to the proximal end thereby establishing a continuous drainage flow path. A medical practitioner may connect the drainage assembly to a patient and establish a flow of drainage fluid into a fluid collection container (initiate the drainage procedure). The medical practitioner may connect a sampling device, such as a syringe, to the sample port of the FFCS and withdraw a sample of drainage fluid. The medical practitioner may activate an occlusion pump coupled to the occlusion port to activate an occlusion mechanism of the flow path through the FFCS and purge fluid from the drainage tube in a single step. Thereafter, the medical practitioner may deactivate the occlusion pump, thereby deactivating the occlusion mechanism and restoring flow through the fluid collection system. The medical practitioner may couple a pressure measurement device to the pressure port of the FFCS to monitor pressure within the flow path. The medical practitioner may configure the pressure measurement device to provide an audio and/or visual indication if the pressure exceeds one or more limits. The medical practitioner may couple a programmable controller to the pressure measurement device and the occlusion pump so that the occlusion pump may be automatically deactivated by a signal from the pressure measurement device. In such an instance, the pressure measurement device may detect a failure of the occlusion mechanism (a non-occluded flow path) and deactivate the occlusion pump, thereby preventing increased pressure from affecting the patient. After purging fluid from the drainage tube, the medical practitioner may deactivate the occlusion pump.

Figure 7:
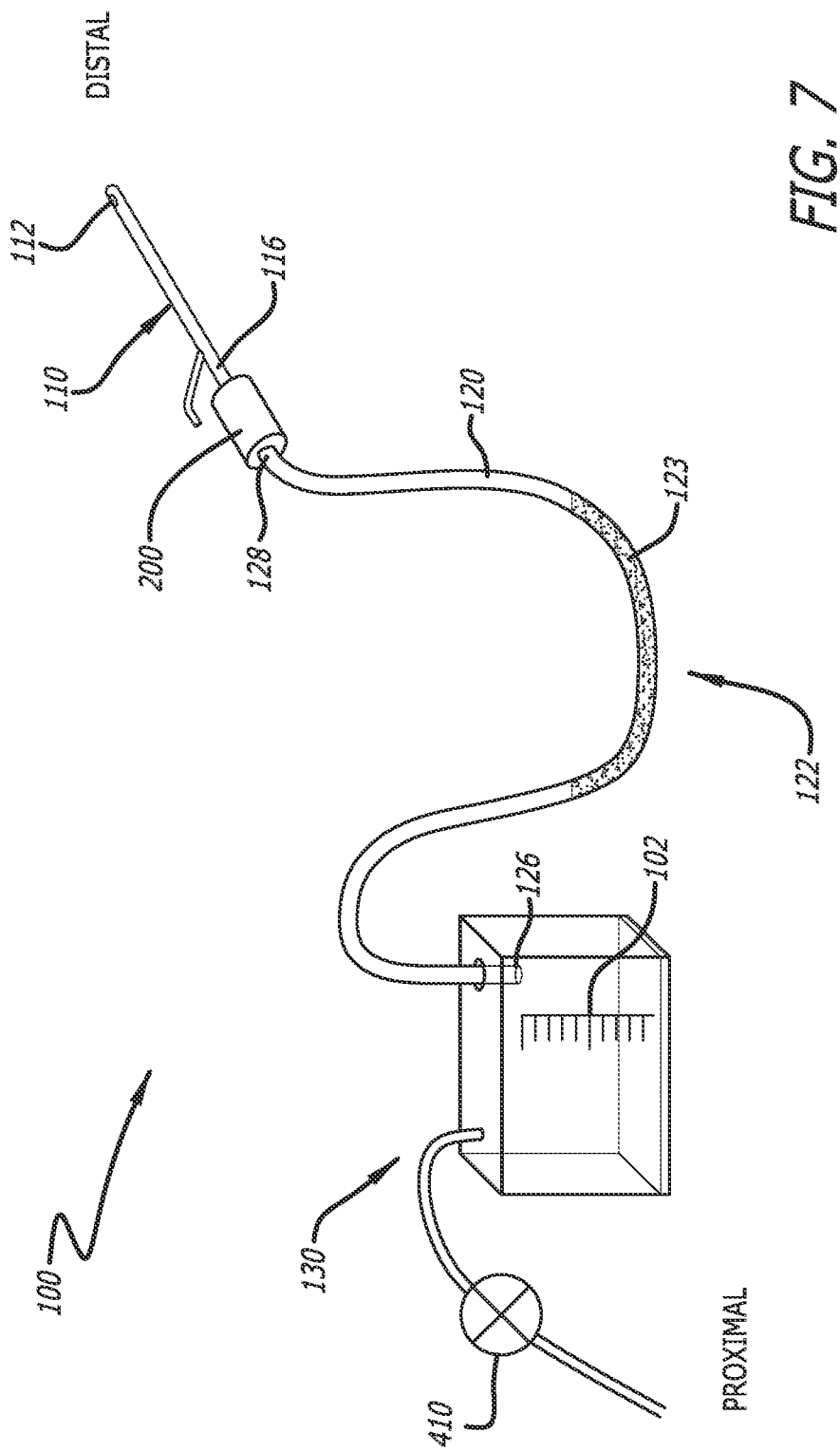
FIG. 7 is an illustration of a fluid flow control system, in accordance with embodiments disclosed herein.

FIG. 7 shows the fluid collection system 100 incorporating the fluid flow control system (FFCS) 200. In some embodiments, the fluid collection system 100 may include an optional vacuum pump 410 fluidly coupled to the container 130. The vacuum pump [210] 410 may aid in purging fluid 123 from the tube 120.

Figure 8:
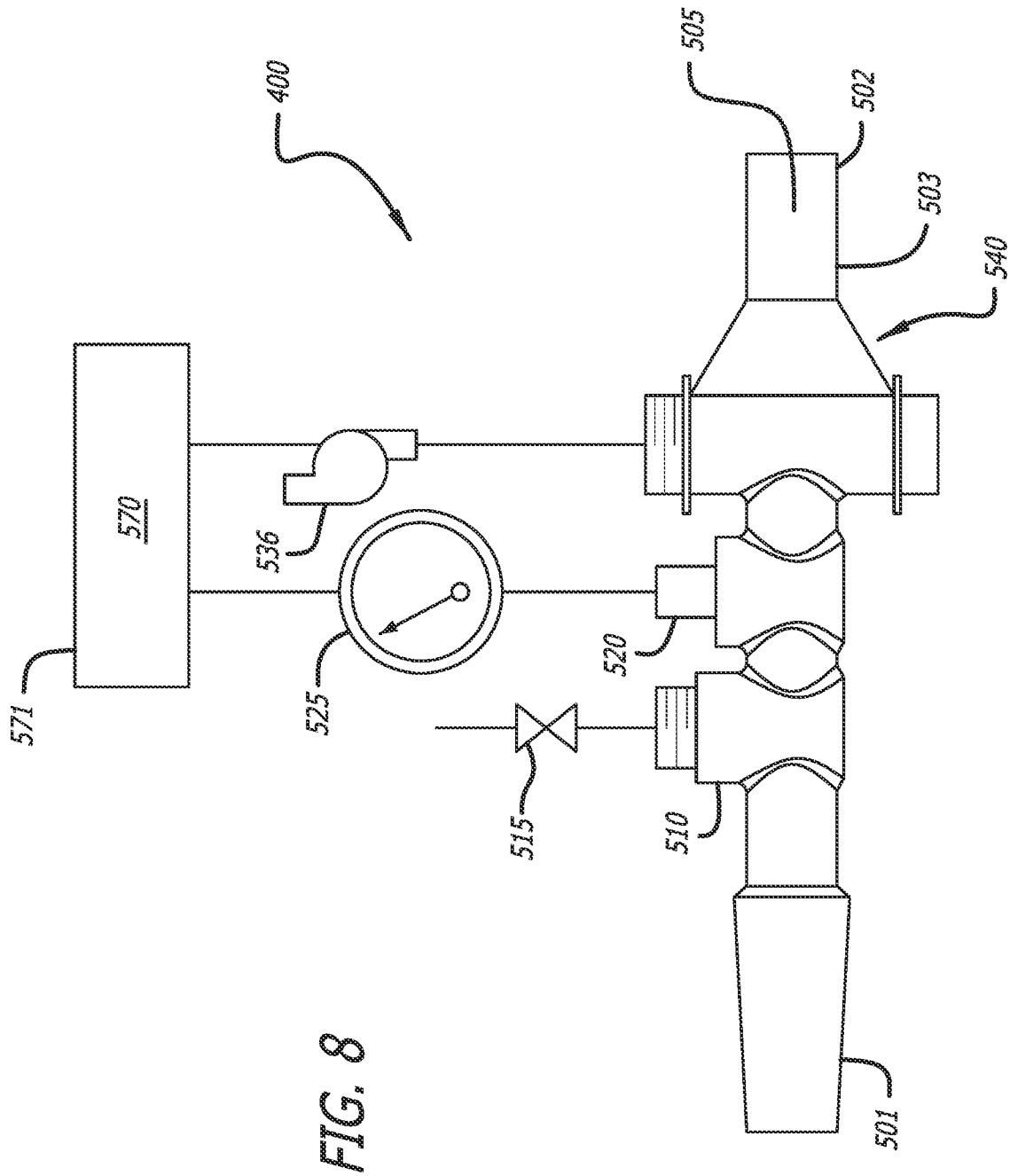
FIG. 8 is an exploded schematic view of a fluid flow control system, in accordance with embodiments disclosed herein.

FIG. 8 illustrates a (FFCS) 400. The FFCS 400 includes a tubular body 503 defining main flow lumen 505 extending from a distal end 501 to a proximal end 502. In use, the fluid 123 flows through the main flow lumen 505. The tubular body 503 may comprise connection features at the distal and proximal ends 501, 502 to facilitate attaching of the tubular body 503 to the catheter 110 and the tube 120. The tubular body 503 may be formed of thermoplastic material such a polycarbonate, nylon, polypropylene, or any other suitable thermoplastic material and may be injection molded. The tubular body 503 may be a single component or formed of multiple components coupled together.

The tubular body 503 may comprise a sample port 510 and a pressure port 520. The sample port 510 may facilitate obtaining a sample of the fluid 123. The sample port 510 may be configured to couple to medical fluid handling components such as tubing, connectors, stopcocks, and syringes. In some embodiments, the sample port 510 may include coupling features consistent with a medical connection standard such as a female Luer standard.

In some embodiments, the sample port 510 may include a manually operated sampling valve 515. The sampling valve 515 may be a separate device coupled to the sample port 510 such as a stopcock or the sampling valve 515 may be formed integral to the sample port 510. The sampling valve 515 may provide for selective opening and closing of the sample port 510. For example, in some instances, the sampling valve 515 may generally remain closed during the drainage process and opened when a sample of fluid 123 is obtained. In some embodiments, the sample port 510 may be omitted.

The pressure port 520 may facilitate measuring the pressure of the fluid 123 within the main flow lumen 505 which may also be indicative of pressure within the catheter 110 and pressure experienced by the patient. In the illustrated embodiment, the pressure port 520 may be disposed proximal the sample port 510. In other embodiments, the pressure port 520 may be disposed distal the sample port 510. In some instances, an elevated pressure at the pressure port 520 may be indicative of potential patient complications such as a drainage flow restriction. As such, measuring the pressure and taking steps to resolve an elevated pressure condition may prevent or resolve patient complications. In some embodiments, the pressure port 520 may be omitted.

The pressure port 520 may be operatively coupled to a pressure measurement device 525. The pressure measurement device 525 may include a pressure transducer fluidly coupled to the main fluid lumen 505 via the pressure port 520 so that the pressure measurement device 525 can provide a pressure measurement of the fluid 123 within the main flow lumen 505 at the location of the pressure port 520. The pressure measurement device 525 may be configured to provide a visual indication of the measured pressure. The pressure measurement device 525 may also be configured to provide audible indication of the measured pressure such as an alarm if the measured pressure exceeds one or more predetermined limits. In some instances, pressure indications from the pressure measurement device 525 may prompt the clinician to take corrective action. The pressure measurement device 525 may also be coupled to a controller 570 including controller logic 571 as further described below. In some embodiments, the pressure measurement device 525 may be omitted.

In some embodiments, the pressure measurement device 525 may be in fluid communication with the main flow lumen 505 via a second fluid. In other words, the second fluid (air) may be disposed between the pressure measurement device 525 and the fluid 123 so that the fluid 123 does not directly contact the pressure measurement device 525. In some embodiments, the fluid 123 may be separated from the pressure measurement device 525 via a flexible member such as a diaphragm. In such embodiments, pressure of the fluid 123 may move the diaphragm which in turn may push on a pressure transducer to facilitate a pressure measurement.

Figure 10A:
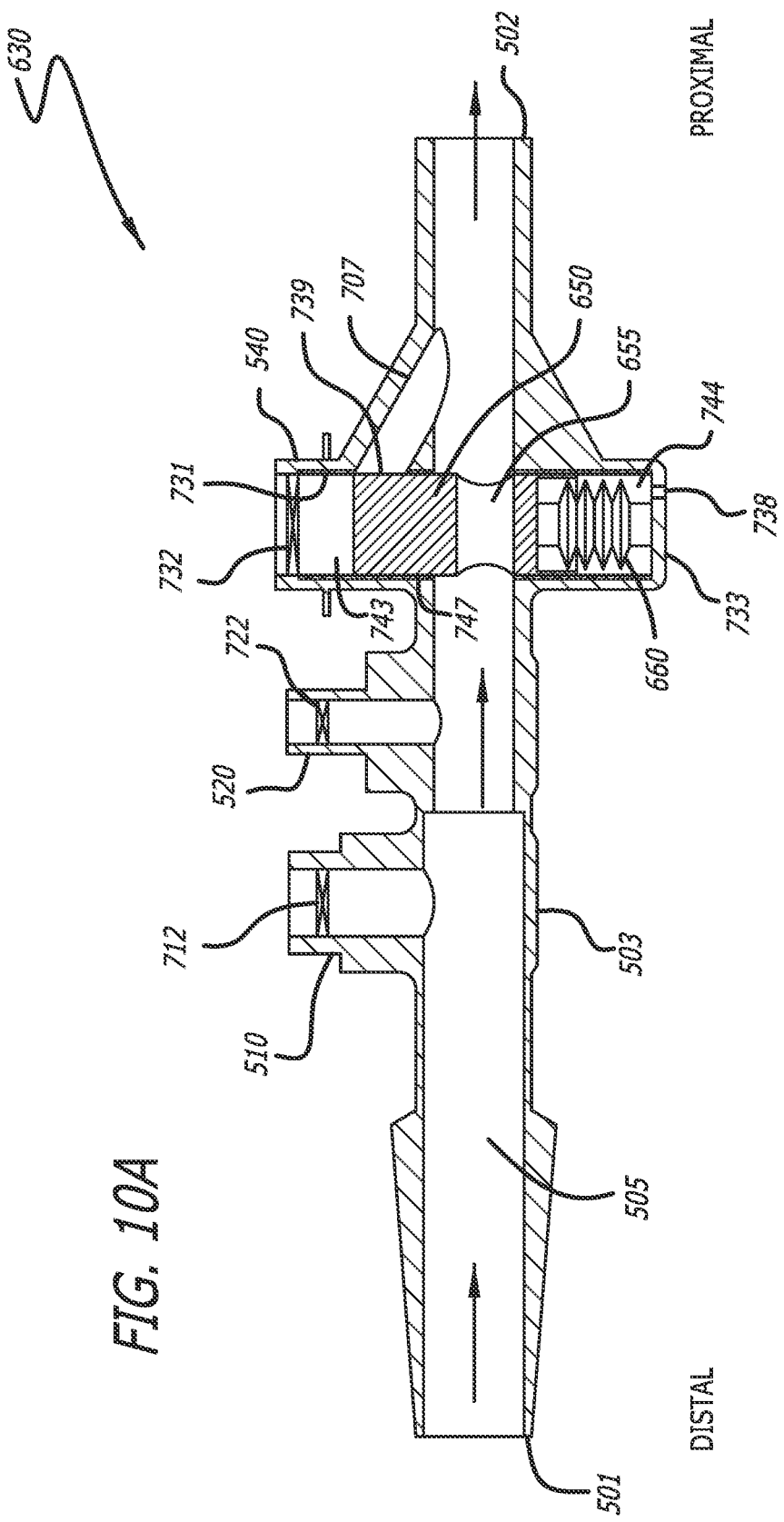
FIG. 10A is cross-sectional view of a portion of the fluid flow control system of FIG. 9 with the valve disposed in a flow configuration, in accordance with embodiments disclosed herein.
Figure 10B:
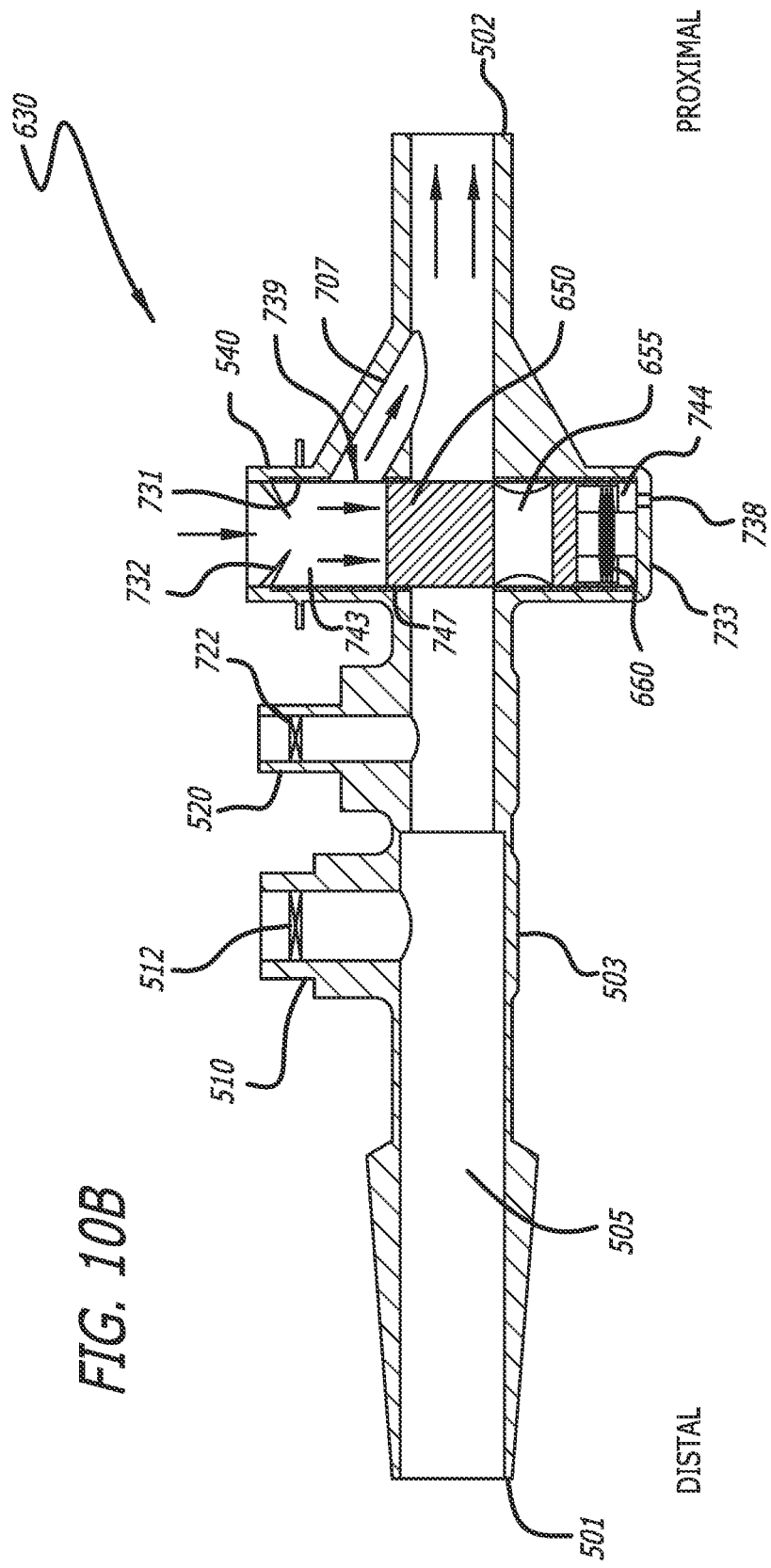
FIG. 10B is cross-sectional view of a portion of the fluid flow control system of FIG. 9 with the valve disposed in purge configuration, in accordance with embodiments disclosed herein.

The FFCS 400 comprises a valve 540 which may be coupled to an airflow source 536. The valve 540 may be selectively disposed between a flow configuration (as illustrated in FIG. 10A) and a purge configuration (as illustrated in FIG. 10B). When disposed in the flow configuration, the valve 540 may: (1) allow flow of fluid 123 through the main flow lumen 305; and (2) isolate the airflow source 536 from the main flow lumen 505. In the purge configuration, the valve 540 may: (1) prevent flow of fluid 123 through the main flow lumen 505; and (2) allow air from the airflow source 536 to flow into the main flow lumen 505. Said another way, the valve 540 may be a three-way valve such that in the flow configuration the tube 120 is in fluid communication with the catheter 110 and in the purge configuration the tube 120 is in fluid communication with the airflow source 536.

The airflow source 536 may be configured to provide an air pressure to the valve 540. The airflow source 536 may be a source of compressed gas, such as a compressed gas bottle, medical compressed air line, an air pump, or the like. The air source 536 may be controllable via an electrical signal, e.g., provided by the controller 570 as determined by the controller logic 571. For example, a source of compressed air may include an electro-mechanical output valve to selectively allow or prevent flow of air from the airflow source 536 to the valve 540. Similarly, an air pump may be turned on and off with the electrical signal.

The valve 540 may be biased toward the flow configuration such that, in the absence of a pressure from the airflow source 536, the valve 540 is disposed in the flow configuration. When a pressure from the airflow source 536 is supplied to the valve 540, the valve 540 may activate toward the purge configuration. In summary, the valve 540 may be in the flow configuration unless a pressure is supplied to the valve 540 in which case the valve 540 is activated into the purge configuration. When the valve 540 is disposed in the purge configuration, airflow from the airflow source 536 may be directed into the main flow lumen 505 at a location proximal the valve 540 which may purge fluid 123 from the tube 120.

The FFCS 400 may include a controller 570. The controller 570 may be a programmable controller including a microprocessor, memory, and an interface comprising one or more digital/analog inputs and outputs. The controller 570 may be configured to continually monitor an input signal, compare the input signal with one or more programmed limits as stored in memory, and provide an output signal. In some embodiments, the controller 570 may be a microcontroller, i.e., a small computer on a single integrated circuit comprising one or more CPUs (processor cores) along with memory and programmable input/output peripherals.

The controller 570 may be electrically coupled to one or both of the pressure measurement device 525 and the airflow source 536. The controller 570 may include controller logic 571 that controls the operation of the airflow source 536. In some embodiments, the controller logic 571 may be defined to detect failures of the valve 540 and initiate a response to prevent a pressure increase in the main flow lumen 505 from reaching the patient. For example, a failure of the valve 540 may allow air from the airflow source 536 to enter the catheter 110 causing a pressure increase within the main flow lumen 505 resulting in potential patient complications. In such an instance, the controller 570 may compare the measured pressure to a predetermined purging pressure limit, and if the measured pressure exceeds the purging pressure limit, the controller 570 may deactivate the airflow source 536, thereby keeping the patient safe from increased pressure.

In some instances, a restriction of flow of fluid 123 through the tube 120, which may be caused by fluid 123 pooling in a dependent loop 122, may cause an increase in the measured pressure. In some embodiments, the controller logic 571 may be defined to detect the increase in pressure and initiate a response to remove the restriction. For example, the controller logic 571 may compare the measured pressure to a predetermined flowing pressure limit, and if the measured pressure exceeds the flowing pressure limit, the controller 570 may activate the airflow source 536 to purge the pooling fluid 123 from the tube 120. In some embodiments, the controller logic 571 may be defined to activate the airflow source 536 to purge the pooling fluid 123 from the tube 120 automatically at specified time intervals. In some embodiments, the flowing pressure limit may be less than the purging pressure limit.

As described above, the fluid collection system 100 may include a vacuum pump coupled to the collection container 130. Applying vacuum to the proximal end of the tube 120 may aid in removing fluid 123 from the tube 120. In some embodiments, the vacuum pump 410 may optionally be coupled to the controller 570 and the controller logic 571 may be defined to activate the vacuum pump 410. In some embodiments, activation of the vacuum pump 410 may be coincident with activation of the airflow soured 536.

Figure 9:
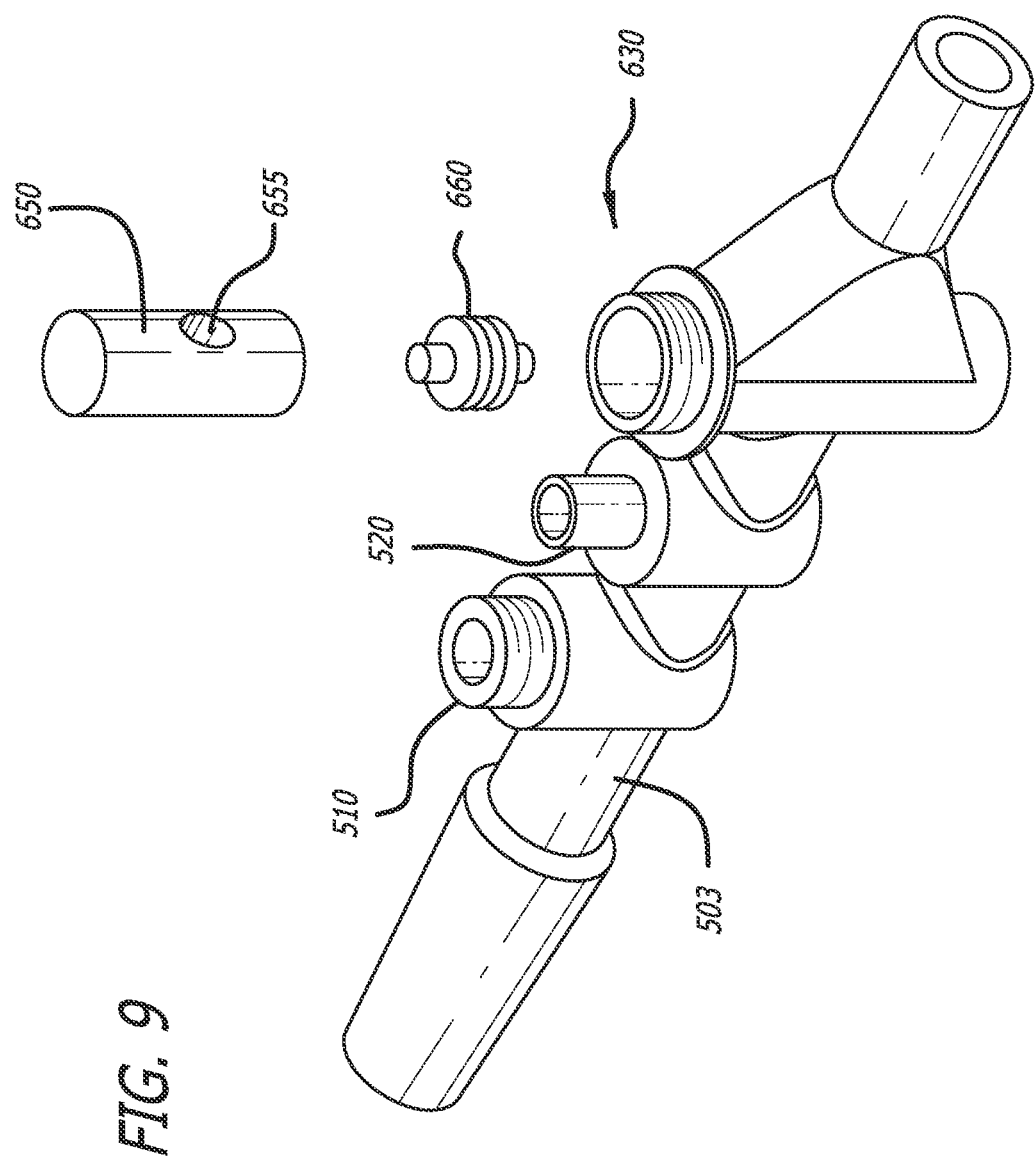
FIG. 9 is an exploded perspective view of a portion of the fluid flow control system in accordance with embodiments disclosed herein.

FIG. 9 is an exploded view of a portion of the FFCS 400. As shown in FIG. 9, the FFCS 400 may include a valve plunger 650 and a biasing member 660, such as a rubber or silicone bellow or a spring mechanism. During assembly of the FFCS 400 the valve plunger 650 and the biasing member 660 may be disposed within a valve chamber 630. The valve plunger 650 includes a lateral lumen 655.

FIGS. 10A and 10B are cross-sectional views of the tubular body 503 including the valve 540. FIG. 10A illustrates the valve 540 in the flow configuration and FIG. 10B illustrates the valve 540 in the purge configuration. The tubular body 503 includes the valve chamber 630. The valve chamber 630 extends across and intersects the main flow lumen 505 such that, absent components within the valve chamber 630, the valve chamber 630 and the main flow lumen 505 are in fluid communication with each other. The valve chamber 630 is open at the top end and closed by a bottom wall 733 at the bottom end. The valve chamber 630 comprises a chamber wall 731 that, in some embodiments, may be cylindrical. The valve chamber 630 is disposed proximal the pressure port 520.

The tubular body 503 includes a purging lumen 707. The purging lumen 707 may facilitate a flow of air into the main flow lumen 505 at a point proximal the valve chamber 630 when the valve 540 is in the purge configuration. The flow of air may purge fluid 123 from the tube 120 such as fluid 123 pooled in a dependent loop 122. The purging lumen 707 extends between the main flow lumen 505 and the valve chamber 630. More specifically, one end of the purging lumen 707 intersects the main flow lumen 505 at a location spaced proximally away from the valve chamber 630 and the other end intersects the valve chamber 630 at a location spaced upward (toward the open end) away from the main flow lumen 505 as shown in FIGS. 10A and 10B. The intersection of the purging lumen 707 with the valve chamber 630 defines a purging lumen port 739.

The valve 540 comprises a valve plunger 650 slidably disposed within the valve chamber 630. The valve plunger 650 may be formed of silicone, ethylene propylene diene monomer (EPDM), rubber, a thermoplastic elastomer (TPE) such as SANTOPRENE™ or any suitably compliant material. The valve plunger 650 is sized and shaped to correspond to the valve chamber 630. More specifically, an outside circumference of the valve plunger 650 is sized and shaped to correspond to an inside circumference of the valve chamber 630 as defined by the chamber wall 731. More specifically still, the outside circumference of the valve plunger 650 may be sized to generate an interference fit with valve chamber 630 so as to form a slidable seal between the valve plunger 650 and the chamber wall 731. In some embodiments, a lubricant 747, such a medical grade silicone oil, may be disposed between the valve plunger 650 and the chamber wall 731. The lubricant 747 may: (1) aid in sealing; and (2) minimize a sliding friction coefficient.

The valve plunger 650 is longitudinally slidable with the valve chamber 630 between an "up" position in accordance with the valve 540 disposed in the flow configuration as shown in FIG. 10A and "down" a position in accordance with the valve 540 disposed in the purge configuration as shown in FIG. 10B. The valve plunger 650 comprises a length from top to bottom that is shorter than a length of the valve chamber 630 from top to bottom. The length of the valve plunger 650 and the length of the valve chamber 630 are correspondingly sized so that the top of the valve plunger 650 is spaced downward away from the open end of the valve chamber 630 when the valve plunger 650 is disposed in the "up" position to define a pressure compartment 743. The length of the valve plunger 650 and the length of the valve chamber 630 are also correspondingly sized so that the bottom of the valve plunger 650 is spaced upward away from the bottom wall 733 of the valve chamber 630 when the valve plunger 650 is disposed in the "down" position to define a lower compartment 744. In some embodiments, the bottom wall 733 may comprise an orifice 738 extending through the bottom wall 733 to allow air to flow into and out of the lower compartment 744 when the valve plunger 650 slides between the "up" the position and the "down" position.

In some embodiments, the valve plunger 650 and valve chamber 630 may comprise corresponding features to constrain movement of the valve plunger 650 within the valve chamber 630. The corresponding features may include mechanical stops to limit longitudinal displace at the "up" and "down" positions. Similarly, the corresponding features may include angular alignment structure such as corresponding longitudinal ribs and grooves to constrain rotation of the valve plunger 650 within the valve chamber 630.

In some instances, it may be advantageous for the clinician to visually ascertain the position of the valve plunger 650 within the valve chamber 630. In some embodiments, the valve 540 may include a visual indication of the position of the valve plunger (up or down). For example, in an embodiment, the valve plunger 650 may include post extending downward from the bottom side of the valve plunger 650 which may visually protrude from the orifice 738 when the valve plunger 650 is in the "down" position.

In another embodiment, the valve chamber wall 731 may include a window to be visually covered or uncovered by the valve plunger 650 to indicate the position of the valve plunger 650.

The valve plunger 650 may be configured to facilitate the valving operation of the valve 540. The valve plunger 650 may comprise a lateral lumen 655 extending laterally through the valve plunger 650. The lateral lumen 655 may align with the main flow lumen 505 when the valve plunger 650 is disposed in the "up" position as shown in FIG. 10A. The valve plunger 650 may also be sized and shaped so as to cover the purging lumen port 739 when the valve plunger 650 is in the "up" position to seal off the purging port 739 and prevent flow of air through the purging lumen 707. Correspondingly, the valve plunger 650 may be sized and shaped so that the lateral lumen 655 does not overlap the main flow lumen 505 when the valve plunger 650 is in the "down" position. As such, the plunger 650 prevents flow of fluid 123 through the main flow lumen 505 when the valve plunger 650 is in the "down" position. More specifically, the valve plunger 650 may be sized and shaped so that the valve plunger 650 occludes the main flow lumen 505 and so that the purging lumen port 739 is uncovered when the valve 540 is in the purging configuration. By way of summary, when the valve 540 is in the flow configuration, the valve plunger 650 is in the "up" position, the lateral lumen 655 is aligned with the main flow lumen 505 allowing flow of fluid 123 through the main flow lumen 505, and the purging lumen port 739 is covered preventing airflow through the purging lumen 707. In contrast, when the valve 540 is in the purge configuration, the valve plunger 650 is in the "down" position, the lateral lumen 655 is not aligned with the main flow lumen 505 preventing flow of fluid 123 through the main flow lumen 505, and the purging lumen port 739 is uncovered allowing air to flow through the purging lumen 707.

The valve 540 may be configured such that during transition from the flow configuration toward the purge configuration, the main flow lumen 505 is occluded to prevent flow of fluid 123 through the main flow lumen 505 before the purging port 739 is uncovered to allow air to flow into the main flow lumen 505. Similarly, the valve 540 may be configured such that during transition from the purge configuration toward the flow configuration, the purging port 739 is covered to prevent flow of air into the main flow lumen 505 before the main flow lumen 505 is non-occluded to allow flow of fluid 123 through the main flow lumen 505.

In the illustrated embodiment, the lateral lumen 655 is shown as an aperture extending laterally through the valve plunger 650. Alternatively, in some embodiments, the valve plunger 650 may comprise an annular groove extending at least partially around the valve plunger 650 or a lateral depression to define a flow lumen extending laterally across the valve plunger 650. As may be appreciated by one of ordinary skill, the valve plunger 650 may comprise any structure that 1) allows flow of fluid 123 through the main flow lumen 505 when the valve plunger 650 is disposed in the "up" position and 2) prevents flow of fluid 123 through the main flow lumen 505 when the valve plunger 650 is disposed in the "down" position.

Similarly, as shown in FIGS. 10A and 10B, the valve plunger 650 is structured so that flow of air through the purging lumen 707 is prevented when a top surface of the valve plunger 650 is disposed above the purging port 739 and flow of air through the purging lumen 707 is allowed when the top surface of the valve plunger 650 is disposed below the purging port 739. Alternatively, in some embodiments, the valve plunger 650 may include a lumen extending through the valve plunger 650 from the top surface to the outside circumference or a longitudinal grove extending from the top surface downward along the outside circumference to provide a lumen for air to flow from the pressure compartment 743 into the purging lumen 707 when the valve plunger 650 is in the "down" position. As may be appreciated by one of ordinary skill, the valve plunger 650 may comprise any structure that 1) prevents fluid flow through the purging lumen 707 when the valve plunger 650 is disposed in the "up" position and 2) allows fluid flow through the purging lumen 707 when the valve plunger 650 is disposed in the "down" position.

The valve 540 may include a biasing member 660. The biasing member 660 may be disposed within the lower compartment 744 and may be operatively coupled to the bottom wall 733 and the valve plunger 650. The biasing member 660 is configured to exert a sufficient upward force on the valve plunger 650 to displace the valve plunger 650 into the "up" position. The biasing member 660 is also configured to allow the valve plunger 650 to be displaced into the "down" position. The biasing member 660 may be of any suitable construction. In some embodiments, the biasing member 660 may be a coil spring, a leaf spring, or any other suitable configuration. In some embodiments, the biasing member 660 may be an integral part of the bottom wall 733 or the valve plunger 650. The biasing member 660 may be formed of an elastomeric, plastic, or metal material. In some instances, it may be advantageous to avoid metal materials since the FFCS 200 may be used near an MRI machine.

In some embodiments, the biasing member 660 may comprise a silicone bellows. In some embodiments, the silicone bellows may be configured to generate a compression force at least partially due to flexing of the circumferential wall. In other embodiments, the silicone bellows may include a closed compartment such that at least a portion of the compression force may be defined by a pressure within the closed compartment. Still, in other embodiments, the compression force may be defined by both flexing of the circumferential wall and pressure within the closed compartment.

In use, a pressure from the airflow source 536 fills the pressure compartment 743 and exerts a downward force on the valve plunger 650 sufficient to overcome the upward force of the biasing member 660 and displace the valve plunger 650 into the "down" position. The airflow source 536 may comprise sufficient capacity (pressure and airflow) to maintain a sufficient downward force on the valve plunger 650 while coincidently delivering sufficient airflow through the purging lumen 707 to purge fluid 123 from the tube 120. The biasing member 660 may provide a sufficient upward force to overcome sliding friction between the valve plunger 650 and the valve chamber wall 731 so as to displace the valve plunger 650 into the "up" position when pressure is removed from the pressure compartment 743. In some embodiments, the purging lumen 707 may include an airflow restriction, such as an orifice, to limit or control airflow through the purging lumen 707.

The sample port 510 may include a vent [712] 512 and the pressure port 520 may include a vent 722 such that fluid flow through each port flows through the vents 512 and 722, respectively. Similarly, the valve chamber 630 may include a vent 732 at its open end so that fluid flow in and out of the valve chamber 630 flows through the vent 732. Each of the vents may be a porous membrane formed of a sintered PTFE, an acrylic copolymer with a nylon backing, or any suitable materials or structures. In some embodiments, one or more vents may be hydrophilic so as to freely allow passage of a liquid. In other embodiments, one or more vents may be hydrophobic so as to inhibit passage of a liquid.

Use of the FFCS 400 may include one or more of the following steps, methods, or processes. A fluid collection system may be assembled by attaching a catheter to the distal end of the FFCS 400 and a drainage tube to the proximal end thereby establishing a continuous drainage flow path. A clinician may connect the drainage assembly to a patient and establish a flow of drainage fluid into a fluid collection container. The clinician may connect a sampling device, such as a syringe, to the sample port of the FFCS and withdraw a sample of drainage fluid. The clinician may activate an airflow source coupled to the valve to transition the valve from the flow configuration to the purging configuration to isolate the drainage tube from the catheter and purge fluid from the drainage tube. In some instances, the clinician may activate a vacuum pump coupled to the collection container to aid in purging drainage fluid from the drainage tube. The clinician may deactivate the airflow source to transition the valve back to the flow configuration and restore flow of fluid from the catheter to the collection container. The clinician may couple a pressure measurement device to the pressure port of the FFCS to monitor pressure within the flow path. The clinician may configure the pressure measurement device to provide an audio and/or visual notification if the pressure exceeds one or more limits. If the clinician is notified that the pressure exceeds one or more limits, the clinician may: (1) activate the airflow source to transition the valve to the purge configuration if the valve is in the flow configuration; or (2) deactivate the airflow source to transition the valve to the flow configuration if the valve is in the purge configuration.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A drainage system, comprising:
   a tubular body including a tubular body lumen and an occlusion side port in fluid communication with the tubular body lumen, wherein the occlusion side port comprises a check valve that permits fluid flow into the tubular body lumen and prevents fluid flow out of the tubular body lumen; and
   a collapsible tube disposed in the tubular body lumen and sealably attached to an inside surface of the tubular body at both a proximal end and a distal end of the collapsible tube;
      wherein a circumference of the collapsible tube at the distal end thereof is sealably attached to the inside surface of the tubular body:
      wherein the occlusion side port is in fluid communication with an outside surface of the collapsible tube, and wherein the occlusion side port is disposed proximal the distal end of the collapsible tube;
      wherein the circumference of the collapsible tube at the proximal end of the collapsible tube is sealably attached to the inside surface of the tubular body forming an annular chamber between the inside surface of the tubular body and the outside surface of the collapsible tube, wherein the occlusion side port is in fluid communication with the annular chamber;

wherein the occlusion side port comprises a relief valve, wherein the relief valve is configured to release pressure from the annular chamber when the relief valve is open; and wherein fluid flow through the tubular body lumen flows through a collapsible tube lumen, wherein the collapsible tube is designed to collapse to a collapsed state to prevent fluid flow through the tubular body lumen, wherein when the collapsible tube is in the collapsed state, the check valve maintains a pressure in the tubular body lumen greater than a pressure within the collapsible tube lumen; and an occlusion fluid pump coupled to the occlusion side port, wherein a flow of fluid through the occlusion side port exerts a force on the outside surface of the collapsible tube causing the collapsible tube to collapse.

2. The drainage system according to claim 1, wherein the force is a side force on the collapsible tube that pushes the collapsible tube toward a side of the tubular body lumen.

3. The drainage system according to claim 2, wherein the fluid is air, wherein an air flow through the occlusion side port defines an air jet exiting the occlusion side port, and wherein the side force is a dynamic pressure defined by a velocity of the air jet impinging on the collapsible tube.

4. The drainage system according to claim 1, wherein fluid flow from the occlusion fluid pump defines pressure within the annular chamber, and wherein the pressure within the annular chamber exerts an inward force on the outside surface of the collapsible tube causing the collapsible tube to collapse.

5. The drainage system according to claim 1, wherein the occlusion side port comprises a porous membrane.

6. The drainage system according to claim 1, further comprising a pressure measurement device operatively coupled to the tubular body via a pressure side port, wherein:

the pressure side port is disposed distal the distal end of the collapsible tube; and the pressure measurement device is configured to measure the pressure within the tubular body lumen.

7. The drainage system according to claim 6, wherein the pressure side port comprises a porous membrane.

8. The drainage system according to claim 6, further comprising a controller coupled to the pressure measurement device and the occlusion fluid pump, wherein the controller is configured to deactivate the occlusion fluid pump in response to a pressure measurement exceeding a first predefined pressure limit.

9. The drainage system according to claim 6, further comprising a purging fluid pump coupled to the tubular body via a purging side port in fluid communication with the tubular body lumen such that fluid flow from the purging fluid pump flows into the tubular body lumen.

10. The drainage system according to claim 9, wherein the purging side port comprises a porous membrane.

11. The drainage system according to claim 9, further including a controller coupled to the purging fluid pump, and wherein the controller is configured to deactivate the purging fluid pump in response to a pressure measurement exceeding a second predefined pressure limit.

12. The drainage system according to claim 1, wherein the tubular body comprises a sample side port in fluid communication with the tubular body lumen, and wherein the sample side port comprises a porous membrane.

13. A method of moving fluid through a drainage lumen, comprising:

collapsing a collapsible tube to a collapsed position, the collapsible tube coupled to an inside surface of a tubular body at both a proximal end and a distal end thereof, the collapsible tube sealably attached along an entire circumference of both the proximal end and the distal end to define an annular chamber between the inside surface of the tubular body and an outside surface of the collapsible tube, the tubular body defining a portion of the drainage lumen, wherein collapsing the collapsible tube includes pumping air by way of an occlusion fluid pump, through an occlusion side port and establishing an occlusion of the drainage lumen, wherein a flow of fluid through the occlusion side port exerts a force on the outside surface of the collapsible tube causing the collapsible tube to collapse, wherein the occlusion side port is in fluid communication with the outside surface of the collapsible tube and the annular chamber, and wherein the occlusion side port is disposed proximal the distal end of the collapsible tube;

pumping air into the drainage lumen through a purging side port of the tubular body proximal the collapsible tube to urge fluid disposed within the drainage lumen in a proximal direction;

maintaining the collapsible tube in the collapsed position by maintaining a pressure in the annular chamber greater than a pressure in the drainage lumen; and subsequent to pumping air into the drainage lumen to urge fluid disposed within the drainage lumen in the proximal direction, actuating a relief valve included with the occlusion side port to release pressure from the annular chamber.

14. The method according to claim 13, further comprising:

measuring a pressure inside the drainage lumen at a position distal the occlusion;

comparing the measured pressure to a predetermined pressure limit; and discontinuing pumping air into the drainage lumen through the purging side port if the measured pressure exceeds the predetermined pressure limit.

15. The method according to claim 13, wherein pumping air through the purging side port defines a dynamic pressure exerting a side force on the collapsible tube to establish the occlusion.

16. The method according to claim 13, wherein a circumference of the collapsible tube at each end of the collapsible tube is sealably coupled to the inside surface of the tubular body to define the annular chamber between the outside surface of the collapsible tube and the inside surface of the tubular body, and wherein pumping air through the occlusion side port into the annular chamber exerts an inward force on the outside surface of the collapsible tube to establish the occlusion.

17. The method according to claim 16, further comprising:

measuring a pressure inside the drainage lumen at a position distal the occlusion;

comparing the measured pressure to a predetermined pressure limit; and discontinuing pumping air through the occlusion side port if the measured pressure exceeds the predetermined pressure limit.

* * * * *